United States Patent

Murata et al.

Patent Number: 5,306,816
Date of Patent: Apr. 26, 1994

[54] PROCESSES FOR PREPARING CARBAPENEM DERIVATIVES

[75] Inventors: Masayoshi Murata, Osaka; Chiyoshi Kasahara, Ikeda; Hideo Tsutsumi, Toyonaka; Yoshihiro Murakami, Takatsuki, all of Japan

[73] Assignee: Fujisawa Pharmaceutical Co., Ltd., Osaka, Japan

[21] Appl. No.: 834,613

[22] Filed: Feb. 12, 1992

[30] Foreign Application Priority Data

Feb. 13, 1991 [GB] United Kingdom ............... 9103034

[51] Int. Cl.$^5$ ............... C07D 205/08; C07D 227/087
[52] U.S. Cl. ..................... 540/200; 540/350
[58] Field of Search ............................. 540/200

[56] References Cited

U.S. PATENT DOCUMENTS

| | | | |
|---|---|---|---|
| 4,772,683 | 9/1988 | Martel | 540/200 |
| 4,816,577 | 3/1989 | Bender | 540/200 |
| 4,983,596 | 1/1991 | Murata | 540/350 |
| 5,075,437 | 12/1991 | Nakai | 540/200 |

FOREIGN PATENT DOCUMENTS

| | | |
|---|---|---|
| 0000828 | 2/1979 | European Pat. Off. . |
| 0037592 | 10/1981 | European Pat. Off. . |
| 0058317 | 8/1982 | European Pat. Off. . |
| 0061205 | 9/1982 | European Pat. Off. . |
| 0102239 | 3/1984 | European Pat. Off. . |
| 2383960 | 10/1978 | France . |
| 2453862 | 11/1980 | France . |

*Primary Examiner*—Mark L. Berch
*Attorney, Agent, or Firm*—Oblon, Spivak, McClelland, Maier & Neustadt

[57] ABSTRACT

The invention relates to carbapenem derivatives useful as antimicrobial agents, more particularly to intermediate compounds for the preparations thereof of the formula

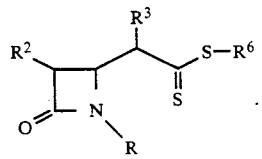

4 Claims, No Drawings

PROCESSES FOR PREPARING CARBAPENEM DERIVATIVES

The present invention relates to novel processes for preparing carbapenem derivatives or salts thereof.

More particularly, it relates to industrially excellent processes for preparing carbapenem derivatives or salts thereof which are useful as antimicrobial agents, to intermediary compounds and salts thereof, and to processes for preparing the intermediary compounds or salts thereof.

The object carbapenem derivatives which can be prepared by the processes of the present invention can be represented by the following general formula (I):

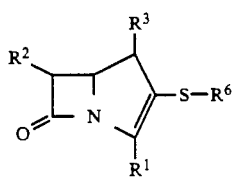

(I)

in which
  $R^1$ is carboxy or protected carboxy,
  $R^2$ is hydroxy(lower)alkyl or protected hydroxy(lower)alkyl,
  $R^3$ is hydrogen or lower alkyl, and
  $R^6$ is an organic group.

In the object compound (I) and the intermediary compounds mentioned below, it is to be understood that there may be one or more stereo-isomeric pair(s) such as optical isomers due to asymmetric carbon atom(s), and such isomers are also included within the scope of the present invention.

According to the present invention, the object compound (I) or salts thereof can be prepared by the processes as illustrated by the following reaction schemes.

Process 1:

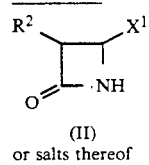 + 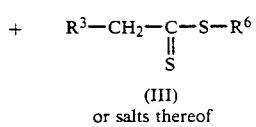

(II) or salts thereof    (III) or salts thereof

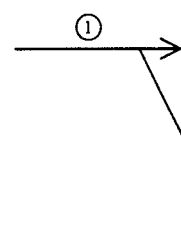

(V) or salts thereof

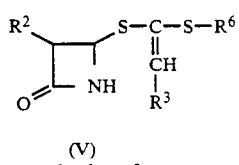

(IV) or salts thereof

Process 2:

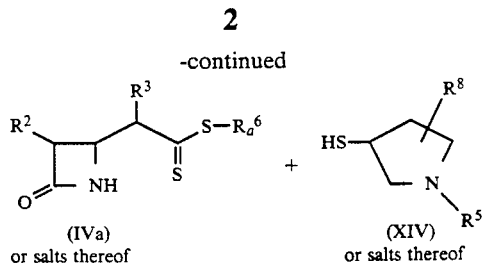

(IVa) or salts thereof    (XIV) or salts thereof

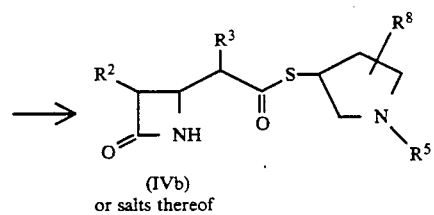

(IVb) or salts thereof

Process 3:

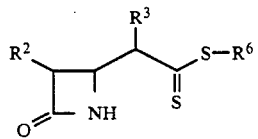

(IV) or salts thereof

① H—C—R¹
(VI)
or its reactive equivalent,
or salts thereof

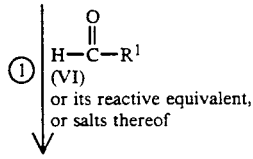

(VII) or salts thereof

② halogenation

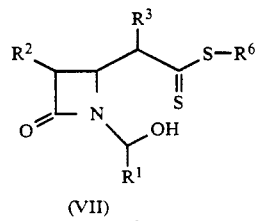

(VIII) or salts thereof

③ P(R⁷)₃
(IX)

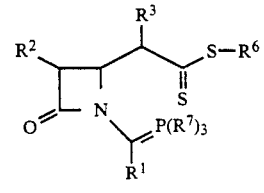

(X) or salts thereof

Process 4:

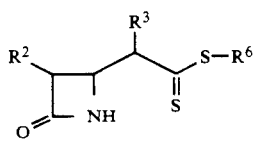

(IV)
or salts thereof

① $X^3-CO-R^1$
(XI)
or salts thereof

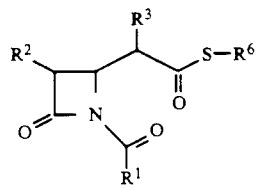

(XII)
or salts thereof

② $P(R^7)_3$
(IX)

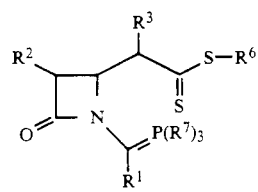

(X)
or salts thereof

Process 5:

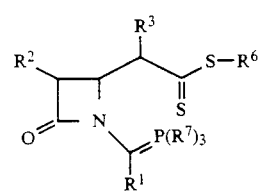

(X)
or salts thereof

↓ cyclization

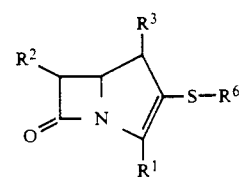

(I)
or salts thereof

Process 6:

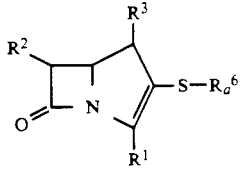

(Ia)
or salts thereof

① Oxidation

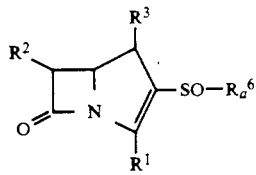

(XIII)
or salts thereof

② $HS$—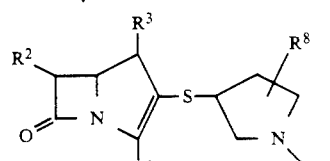
(XIV)
or salts thereof

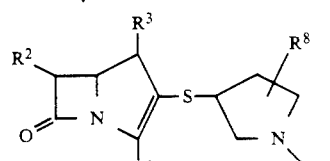

(Ib)
or salts thereof

Process 7:

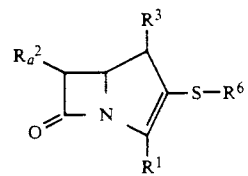

(Ic)
or salts thereof

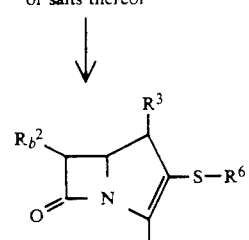

(Id)
or salts thereof wherein
$R^1$, $R^2$, $R^3$ and $R^6$ are each as defined above,
$X^1$ is a leaving group,
$X^2$ is halogen,
$X^3$ is an acid residue, $R^7$ is lower alkoxy or aryl, $R^5$ is hydrogen, lower alkanimidoyl, lower cycloalkenyl which may have suitable substituent(s) or imino-protective group, $R^8$ is carbamoyl which may have one or two suitable substituent(s), or a group of the formula:

—A—X—$R^4$ (in which $R^4$ is lower alkyl having suitable substituent(s), heterocyclic group optionally substituted by suitable substituent(s), or lower alkylsulfonyl, A is lower alkylene, and X is sulfur, oxygen, imino or protected $R_a^6$ group other than the group of the formula:

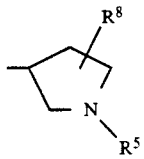

(in which $R^5$ and $R^8$ are each as defined above), $R_a^2$ is protected hydroxy(lower)alkyl, and $R_b^2$ is hydroxy(lower)alkyl.

Suitable salts of the object compound (I) are conventional non-toxic salts and may include a salt with a base such as an inorganic base salt, for example, an alkali metal salt (e.g. sodium salt, potassium salt, etc.), an alkaline earth metal salt (e.g. calcium salt, magnesium salt, etc.), an ammonium salt, an organic base salt, for example, an organic amine salt (e.g. triethylamine salt, pyridine salt, picoline salt, ethanolamine salt, triethanolamine salt, dicyclohexylamine salt, N,N'-dibenzylethylenediamine salt, dibenzylamine salt, etc.); a salt with an acid such as an inorganic acid addition salt (e.g. hydrochloride, hydrobromide, sulfate, phosphate, etc.), an organic acid addition salt (e.g. formate, acetate, trifluoroacetate, maleate, tartrate, methanesulfonate, benzenesulfonate, toluenesulfonate, etc.); a salt with a basic or acidic amino acid (e.g. arginine, aspartic acid, glutamic acid, etc.); an intermolecular quaternary salt, and the like.

In the above and subsequent descriptions of the present specification, suitable examples and illustrations of the various definitions which the present invention includes within the scope thereof are explained in detail as follows.

The term "lower" is intended to mean 1 to 6 carbon atom(s), unless otherwise indicated.

Suitable "protected carboxy" may include esterified carboxy wherein "esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester, t-butyl ester, pentyl ester, hexyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1-(or 2-)acetoxyethyl ester, 1-(or 2- or 3-)acetoxypropyl ester, 1-(or 2- or 3- or 4-)acetoxybutyl ester, 1-(or 2-)propionyloxyethyl ester, 1-(or 2- or 3-)propionyloxypropyl ester, 1-(or 2-)butyryloxyethyl ester, 1-(or 2-)isobutyryloxyethyl ester, 1-(or 2-)pyvaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, 1-(or 2-)pentanoyloxyethyl ester, etc.], lower alkanesulfonyl(lower)alkyl ester (e.g. 2-mesylethyl ester, etc.), mono(or di or tri)halo(lower)alkyl ester (e.g. 2-iodoethyl ester, 2,2,2-trichloroethyl ester, etc.); lower alkoxycarbonyloxy(lower)alkyl ester [e.g. methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-)isopropoxycarbonyloxyethyl ester, etc.], phthalidylidene(lower)alkyl ester, or (5-lower alkyl-2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) such as mono- or di- or triphenyl(lower)alkyl ester which may have halogen or lower alkoxy (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have at least one suitable substituent(s) (e.g. phenyl ester, 4-chlorophenyl ester, tolyl ester, t-butylphenyl ester, xylyl ester, mesityl ester, cumenyl ester, etc.); phthalidyl ester; and the like.

More preferable example of the protected carboxy thus defined may be $C_2$–$C_4$ alkenyloxycarbonyl and phenyl(or nitrophenyl)($C_1$–$C_4$)alkoxycarbonyl.

Suitable "hydroxy(lower)alkyl" and hydroxy(lower)alkyl in the embodiment of "lower alkyl having suitable substituent(s)" may include straight or branched lower alkyl having hydroxy group such as hydroxymethyl, hydroxyethyl, hydroxypropyl, 1-(hydroxymethyl)ethyl, 1-hydroxy-1-methylethyl, hydroxybutyl, hydroxypentyl, hydroxyhexyl, and the like, in which more preferable example may be hydroxy($C_1$–$C_4$)alkyl.

Suitable "protected hydroxy(lower)alkyl" and protected hydroxy(lower)alkyl in the embodiment of "lower alkyl having suitable substituent(s)" means aforementioned hydroxy(lower)alkyl, in which the hydroxy group is protected by a conventional hydroxy-protective group such as those mentioned in the explanation of imino-protective group as mentioned below; ar(lower)alkyl such as mono- or di- or triphenyl(lower)alkyl (e.g. benzyl, benzhydryl, trityl, etc.), etc.; trisubstituted silyl such as tri(lower)alkylsilyl (e.g. trimethylsilyl, triethylsilyl, isopropyldimethylsilyl, t-butyldimethylsilyl, diisopropylmethylsilyl, etc.), triarylsilyl (e.g. triphenylsilyl, etc.), triar(lower)alkylsilyl (e.g. tribenzylsilyl, etc.), etc.; and the like.

More preferable example of "protected hydroxy(lower)alkyl thus defined may be [phenyl(or nitrophenyl)($C_1$–$C_4$)alkoxy]carbonyloxy($C_1$–$C_4$)alkyl, ($C_2$–$C_4$)alkenyloxycarbonyloxy($C_1$–$C_4$)alkyl and [tri($C_1$–$C_4$)alkylsilyl]oxy($C_1$–$C_4$)alkyl.

Suitable "lower alkyl" may include straight or branched one such as methyl, ethyl, propyl, isopropyl, butyl, t-butyl, pentyl, hexyl, and the like, in which more preferable example may be $C_1$–$C_4$ alkyl.

Suitable "organic group" may include lower alkyl as mentioned above, mono(or di or tri)halo(lower)alkyl (e.g. chloromethyl, dichloromethyl, trichloromethyl, bromomethyl, chloroethyl, dichloroethyl, trichloroethyl, fluoroethyl, trifluoroethyl, etc.), lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1 or 2 or 3 butynyl, 1 or 2 or 3 or 4-pentynyl, 1 or 2 or 3 or 4 or 5-hexynyl, etc.), aryl which may have one or more (preferably one to three) suitable substituent(s), ar(lower)alkyl such as phenyl(-lower)alkyl (e.g., benzyl, phenethyl, phenylpropyl, etc.), heterocyclic group which may have one or more (preferably one to three) suitable substituent(s), and the like.

Suitable "leaving group" may include ar(lower)alkoxy such as phenyl(lower)alkoxy (e.g. benzyloxy, etc.), etc.; lower alkoxy (e.g. ethoxy, etc.); halogen (e.g. chlorine, bromine, iodine, etc.); acyloxy such as lower alkanoyloxy (e.g. acetoxy, etc.), sulfonyloxy (e.g. methanesulfonyloxy, benzenesulfonyloxy, toluenesulfonyloxy, etc.), etc.; or the like.

Suitable "halogen" may include chlorine, bromine, iodine and fluorine.

Suitable "acid residue" may include an inorganic acid residue such as azide, halogen (e.g. chlorine, bromine, fluorine or iodine), and the like, an organic acid residue such as acyloxy (e.g. benzenesulfonyloxy, tosyloxy, methanesulfonyloxy, acetoxy, etc.), and the like, in which more preferable example may be halogen.

Suitable "lower alkoxy" may include straight or branched one such as methoxy, ethoxy, propoxy, isopropoxy, butoxy, isobutoxy, pentyloxy, isopentyloxy, hexyloxy, etc., in which more preferable example may be $C_1-C_4$ alkoxy.

Suitable "aryl" may include phenyl, naphthyl and the like.

Suitable "substituent" in the term "aryl which may have one or more suitable substituent(s)" may include lower alkyl as exemplified above, halogen as exemplified above, hydroxy, protected hydroxy, lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1 or 2 or 3 butynyl, 1 or 2 or 3 or 4-pentynyl, 1 or 2 or 3 or 4 or 5-hexynyl, etc.), and the like.

Suitable "lower alkyl having suitable substituent(s)" may include protected or unprotected hydroxy(lower)alkyl; protected or unprotected hydroxy(lower)alkyl having protected or unprotected amino; halo(lower)alkyl; protected or unprotected carbamoyl(lower)alkyl; protected or unprotected amino(lower)alkyl; protected or unprotected ureido(lower)alkyl; protected or unprotected ureidocarbonyl(lower)alkyl; triazolyl(lower)alkyl;

mono- or di(lower)alkylamino(lower)alkyl; protected mono(lower)alkylamino(lower)alkyl;

mono- or di(lower)alkylcarbamoyl(lower)alkyl; protected or unprotected carboxy(lower)alkyl; and the like.

Suitable protected or unprotected hydroxy(lower)alkyl having protected or unprotected amino means aforementioned hydroxy(lower)alkyl having amino group such as 1-amino-1-hydroxymethyl, 2-amino-1-hydroxyethyl, 1-amino-2-hydroxyethyl, 3-amino-2-hydroxypropyl, 2-amino-3-hydroxypropyl, 4-amino-3-hydroxybutyl, 5-amino-4-hydroxypentyl, 6-amino-5-hydroxyhexyl, and the like, in which the amino and/or hydroxy group(s) may be protected by a conventional amino- and/or hydroxy-protective group(s) as mentioned below or above.

More preferable example of protected or unprotected hydroxy(lower)alkyl which has protected or unprotected amino thus defined may be hydroxy($C_1-C_4$)alkyl having amino or phenyl(or nitrophenyl)($C_1-C_4$)alkoxycarbonylamino.

Suitable "halo(lower)alkyl" may include straight or branched lower alkyl having at least one (preferably one to three) halogen (e.g. chlorine, bromine, iodine, fluorine) such as chloromethyl, fluoromethyl, bromomethyl, iodomethyl, chloroethyl, bromoethyl, fluoroethyl, 1-(chloromethyl)ethyl, 1-(fluoromethyl)ethyl, chloropropyl, fluoropropyl, fluorobutyl, fluoropentyl, fluorohexyl, dichloromethyl, dibromomethyl, diiodomethyl, difluoromethyl, trifluoromethyl, chloroethyl, chlorofluoroethyl, difluoroethyl, trifluoroethyl, chloropropyl, difluoropropyl, trichlorobutyl, chloropentyl, chlorohexyl, and the like, in which more preferable example may be monohalo($C_1-C_4$)alkyl.

Suitable "carbamoyl(lower)alkyl" may include straight or branched lower alkyl having carbamoyl group such as carbamoylmethyl, carbamoylethyl, carbamoylpropyl, 1-(carbamoylmethyl)ethyl, 1-carbamoyl-1-methylethyl, carbamoylbutyl, carbamoylpentyl, carbamoylhexyl, and the like, in which more preferable example may be carbamoyl($C_1-C_4$)alkyl.

Suitable "protected carbamoyl(lower)alkyl" means aforementioned carbamoyl(lower)alkyl, in which the carbamoyl group is protected by a conventional carbamoyl-protective group such as mono(or di or tri)-halo(lower)alkanoyl (e.g. trichloroacetyl, etc.), ar(lower)alkyl which may have suitable substituent(s), for example, mono(or di or tri)phenyl(lower)alkyl (e.g. benzyl, phenethyl, benzhydryl, trityl, etc.), mono(or di)lower alkoxyphenyl(lower)alkyl (e.g. 2,4-dimethoxybenzyl, etc.), bis(lower alkoxyphenyl)(lower)alkyl [e.g. bis(4-methoxyphenyl)methyl, etc.], halosulfonyl (e.g. chlorosulfonyl, etc.), and the like, in which more preferable one may be trihalo($C_1-C_4$)alkanoyl, bis[($C_1-C_4$)alkoxyphenyl]($C_1-C_4$)alkyl and halosulfonyl.

More preferable example of "protected carbamoyl(lower)alkyl" thus defined may be trihalo($C_1-C_4$)alkanoylcarbamoyl($C_1-C_4$)alkyl, N-[bis{($C_1-C_4$)alkoxyphenyl}($C_1-C_4$)alkyl]carbamoyl($C_1-C_4$)alkyl and halosulfonylcarbamoyl($C_1-C_4$)alkyl.

Suitable "amino(lower)alkyl" may include straight or branched lower alkyl having amino group such as aminomethyl, 1-(or 2-)aminoethyl, aminopropyl, aminobutyl, 2-amino-1,1-dimethylethyl, 1-(or 2- or 3-)amino-1-(or 2-)methylpropyl, aminopentyl, aminohexyl, and the like, in which more preferable example may be amino($C_1-C_4$)alkyl.

Suitable "protected amino(lower)alkyl" means aforementioned amino(lower)alkyl, in which the amino group is protected by a conventional amino-protective group such as those mentioned in the explanation of protected hydroxy(lower)alkyl as mentioned above, in which more preferable example may be phenyl(or nitrophenyl)($C_1-C_4$)alkoxycarbonyl and $C_1-C_4$ alkylsulfonyl.

More preferable example of "protected amino(lower)alkyl" thus defined may be N-[phenyl(or nitrophenyl)($C_1-C_4$)alkoxycarbonyl]amino($C_1-C_4$)alkyl and ($C_1-C_4$)alkylsulfonylamino($C_1-C_4$)alkyl.

Suitable "ureido(lower)alkyl" may include straight or branched lower alkyl having ureido group, such as ureidomethyl, ureidoethyl, ureidopropyl, 1-(ureidomethyl)ethyl, 1-ureido-1-methylethyl, ureidobutyl, 1,1-dimethyl-2-ureidoethyl, ureidopentyl, ureidohexyl, and the like, in which more preferable example may be ureido($C_1$-$C_4$)alkyl.

Suitable "protected ureido(lower)alkyl" means aforementioned ureido(lower)alkyl, in which the ureido group is protected by a conventional ureido-protective group such as ar(lower)alkyl which may have suitable substituent(s), for example, mono(or di or tri)phenyl(lower)alkyl (e.g. benzyl, phenethyl, benzhydryl, trityl, etc.), mono(or di)lower alkoxyphenyl(lower)alkyl (e.g. 2,4-dimethoxybenzyl, etc.) bis(lower alkoxyphenyl)(lower)alkyl [e.g. bis(4-methoxyphenyl)methyl, etc.], and the like, in which more preferable one may be phenyl($C_1$-$C_4$)alkyl.

Suitable "ureidocarbonyl(lower)alkyl" may include straight or branched lower alkyl having ureidocarbonyl group, such as ureidocarbonylmethyl, ureidocarbonylethyl, ureidocarbonylpropyl, 1-(ureidocarbonylmethyl)ethyl, 1-ureidocarbonyl-1-methylethyl, ureidocarbonylbutyl, 1,1-dimethyl-2-ureidocarbonylethyl, ureidocarbonylpentyl, ureidocarbonylhexyl, and the like.

Suitable "protected ureidocarbonyl(lower)alkyl" means aforementioned ureidocarbonyl(lower)alkyl, in which the ureido group is protected by a conventional ureido-protective group such as ar(lower)alkyl which may have suitable substituent(s), for example, mono(or di or tri)phenyl(lower)alkyl (e.g. benzyl, phenethyl, benzhydryl, trityl, etc.), mono(or di)lower alkoxyphenyl(lower)alkyl (e.g. 2,4-dimethoxybenzyl, etc.), bis(lower alkoxyphenyl)(lower)alkyl [e.g. bis(4-methoxyphenyl)methyl, etc.], and the like, in which more preferable one may be phenyl($C_1$-$C_4$)alkyl.

Suitable "triazolyl(lower)alkyl" may include straight or branched lower alkyl having triazolyl group such as triazolylmethyl, triazolylethyl, triazolylpropyl, 1-(triazolylmethyl)ethyl, 1-triazolyl-1-methylethyl, triazolylbutyl, triazolylpentyl, triazolylhexyl, and the like, in which more preferable example may be triazolyl($C_1$-$C_4$)alkyl.

Suitable "mono- or di(lower)alkylamino(lower)alkyl" means straight or branched lower alkyl as mentioned above, which has straight or branched, mono- or di(lower)alkylamino group such as methylamino, dimethylamino, ethylamino, diethylamino, N-methyl-N-ethylamino, propylamino, dipropylamino, isopropylamino, butylamino, pentylamino, hexylamino, and the like. More preferable example of mono- or di(lower)alkylamino(lower)alkyl thus defined may be mono- or di($C_1$-$C_4$)alkylamino($C_1$-$C_4$)alkyl.

Suitable "protected mono(lower)alkylamino(lower)alkyl means aforementioned mono(lower)alkylamino(lower)alkyl, in which the amino group is protected by a conventional amino-protective group such as those exemplified for the hydroxy-protective group in the explanation of the "protected hydroxy(lower)alkyl" as mentioned above, wherein more preferable example of amino-protective group may be phenyl(or nitrophenyl)($C_1$-$C_4$)alkoxycarbonyl.

Preferable example of protected mono(lower)alkylamino(lower)alkyl thus defined may be N-(lower)alkyl-N-nitrophenyl(lower)alkoxycarbonylamino(lower)alkyl and more preferable one may be N-($C_1$-$C_4$)alkyl-N-(4-nitrobenzyloxycarbonyl)amino($C_1$-$C_4$)alkyl.

Suitable "mono- or di(lower)alkylcarbamoyl(lower)alkyl" means straight or branched lower alkyl as mentioned above, which has straight or branched, mono- or di(lower)alkylcarbamoyl group such as methylcarbamoyl, dimethylcarbamoyl, ethylcarbamoyl, diethylcarbamoyl, N-methyl-N-ethylcarbamoyl, propylcarbamoyl, dipropylcarbamoyl, isopropylcarbamoyl, butylcarbamoyl, pentylcarbamoyl, hexylcarbamoyl, and the like.

More preferable example of mono- or di(lower)alkylcarbamoyl(lower)alkyl thus defined may be mono- or di($C_1$-$C_4$)alkylcarbamoyl($C_1$-$C_4$)alkyl.

Suitable "carboxy(lower)alkyl" means straight or branched lower alkyl as mentioned above, which has carboxy group such as carboxymethyl, carboxyethyl, carboxypropyl, 1-(carboxymethyl)ethyl, 1-carboxy-1-methylethyl, carboxybutyl, carboxypentyl, carboxyhexyl, and the like, in which more preferable example may be carboxy($C_1$-$C_4$)alkyl.

Suitable "protected carboxy(lower)alkyl" means aforementioned carboxy(lower)alkyl, in which the carboxy group is protected by a conventional carboxy-protective group to form so-called "esterified carboxy" as exemplified in the explanation of "protected carboxy" as mentioned above. Preferable example of protected carboxy(lower)alkyl thus defined may be lower alkenyloxycarbonyl(lower)alkyl and mono- or di- or triphenyl(lower)alkoxycarbonyl(lower)alkyl, which may have nitro or lower alkoxy, more preferable one may be ($C_2$-$C_4$)alkenyloxycarbonyl($C_1$-$C_4$)alkyl and phenyl(or nitrophenyl)($C_1$-$C_4$)alkoxycarbonyl($C_1$-$C_4$)alkyl.

Suitable "heterocyclic group" may include saturated or unsaturated, monocyclic or polycyclic heterocyclic group containing at least one hetero-atom such as oxygen, sulfur and nitrogen atom.

Preferable heterocyclic group may be unsaturated, 3 to 8-membered, more preferably 5 or 6-membered, heteromonocyclic group containing 1 to 4 nitrogen atom(s), for example pyrrolyl, pyrrolinyl, imidazolyl, imidazolinyl, pyrazolyl, pyrazolinyl, pyridyl, pyridyl N-oxide, pyridinio, dihydropyridyl, tetrahydropyridyl [e.g. 1,2,3,6-tetrahydropyridyl, etc.], pyrimidinyl, pyrimidinio, pyrazinyl, pyrazinio, pyridazinyl, pyridazinio, triazinyl [e.g. 1,3,5-triazinyl, 1,2,4-triazinyl and 1,2,3-triazinyl], tetrahydrotriazinyl [e.g. 1,2,5,6-tetrahydro-1,2,4-triazinyl, 1,4,5,6-tetrahydro-1,2,4-triazinyl, etc.], triazinio, triazolyl [e.g. 1H-1,2,4-triazolyl, 1H-1,2,3-triazolyl, 2H-1,2,3-triazolyl, etc.], triazolio, tetrazinyl, tetrazinio, tetrazolyl [e.g. 1H-tetrazolyl and 2H-tetrazolyl], tetrazolio, etc.;

saturated, 3 to 8-membered, more preferably 5 or 6-membered heteromonocyclic group containing 1 to 4 nitrogen atom(s), for example, pyrrolidinyl, imidazolidinyl, piperidino, piperazinyl, etc.;

unsaturated, 3 to 8-membered, more preferably 5 or 6-membered, heteromonocyclic group containing 1 to 2 sulfur atom(s) and 1 to 3 nitrogen atom(s), for example, thiazolyl, thiazolio, isothiazolyl, thiadiazolyl [e.g. 1,2,3-thiadiazolyl, 1,2,4-thiadiazolyl, 1,3,4-thiadiazolyl, 1,2,5-thiadiazolyl], thiadiazolio, thiazolinyl, dihydrothiazinyl, etc.; or the like.

Suitable "substituent" in the term "heterocyclic group optionally substituted by suitable substituent(s)" may include lower alkyl (e.g. methyl, ethyl, propyl, isopropyl, butyl, isobutyl, pentyl, hexyl, etc.); amino or amino(lower)alkyl [e.g. aminomethyl, 1-(or 2-)aminoethyl, aminopropyl, aminobutyl, 1-(or 2- or 3-)amino-1-(or 2-)methylpropyl, aminopentyl, aminohexyl, etc.], in which said amino moiety may be substituted by one or two lower alkyl group(s) as mentioned above; and the like, and further, in case that the heterocyclic group is pyrrolidinyl, the imino-moiety of pyrrolidine ring may be protected by a conventional imino-protective group as mentioned below.

More preferable example of "heterocyclic group optionally substituted by suitable substituent(s)" may be saturated or unsaturated 5 or 6-membered heteromonocyclic group containing 1 to 4 nitrogen atom(s), or containing 1 to 2 sulfur atom(s) and 1 to 3 nitrogen atom(s), which may have $C_1$-$C_4$ alkyl, N,N-di($C_1$-$C_4$)alkylamino($C_1$-$C_4$)alkyl or phenyl(or nitrophenyl)($C_1$-$C_4$)alkoxycarbonyl.

Suitable "substituent" in the term "heterocyclic group which may have one or more suitable substituent(s)" may include lower alkyl as exemplified above, carbamoyl which may have one or two suitable substituent(s), lower alkanimidoyl, lower cycloalkenyl which may have suitable substituent(s), lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1 or 2 or 3 butynyl, 1 or 2 or 3 or 4-pentynyl, 1 or 2 or 3 or 4 or 5-hexynyl, etc.), a group of the formula: —A—X—$R^4$ (in which A, X and $R^4$ are each as defined above), and the like, and further, in case that the heterocyclic group is pyrrolidinyl, the imino-moiety of pyrrolidine ring may be protected by a conventional imino-protective group as mentioned below.

More preferable example of "heterocyclic group which may have one or more suitable substituent(s)" may be a group of the formula:

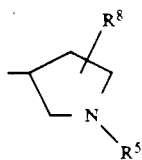

(wherein $R^8$ and $R^5$ are each as defined above).

Suitable "substituent" in the term "carbamoyl which may have one or two suitable substituent(s)" may include lower alkyl as exemplified above, lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1 or 2 or 3 butynyl, 1 or 2 or 3 or 4-pentynyl, 1 or 2 or 3 or 4 or 5-hexynyl, etc.), and the like.

Suitable "lower alkylsulfonyl" may include methylsulfonyl, ethylsulfonyl, propylsulfonyl, butylsulfonyl, pentylsulfonyl, hexylsulfonyl, and the like, in which more preferable example may be ($C_1$-$C_4$)alkylsulfonyl.

Suitable "lower alkanimidoyl" may be straight or branched one such as formimidoyl, acetimidoyl, propionimidoyl, butyrimidoyl, isovalerimidoyl, pentanimidoyl, hexanimidoyl, and the like, in which more preferable one may be ($C_1$-$C_4$)alkanimidoyl.

Suitable "lower cycloalkenyl" moiety of "lower cycloalkenyl which may have suitable substituent(s)" may be $C_3$-$C_6$ cycloalkenyl such as cyclopropenyl, cyclobutenyl, cyclopentenyl, cyclohexenyl, cyclopentadienyl, cyclohexadienyl, and the like, wherein said lower cycloalkenyl moiety may have suitable substituent(s) such as oxo, amino, protected amino wherein the amino-protective group is as mentioned above, and the like.

More preferable example of "lower cycloalkenyl which may have suitable substituents "thus defined may be 3-oxo-1-cycloalken-1-yl having $C_4$-$C_6$ carbon atoms, which may be substituted by suitable substituent(s) selected from a group consisting of amino and oxo.

Suitable "imino-protective group" may include acyl such as carbamoyl, aliphatic acyl, aromatic acyl, heterocyclic acyl and aliphatic acyl substituted with aromatic or heterocyclic group(s) derived from carboxylic carbonic, sulfonic and carbamic acids.

The aliphatic acyl may include saturated or unsaturated, acyclic or cyclic ones, for example, alkanoyl such as lower alkanoyl (e.g. formyl, acetyl, propionyl, butyryl, isobutyryl, valeryl, isovaleryl, pivaloyl, hexanoyl, etc.), alkylsulfonyl such as lower alkylsulfonyl (e.g. mesyl, ethylsulfonyl, propylsulfonyl, isopropylsulfonyl, butylsulfonyl, isobutylsulfonyl, pentylsulfonyl, hexylsulfonyl, etc.), carbamoyl, N-alkylcarbamoyl (e.g. methylcarbamoyl, ethylcarbamoyl, etc.), alkoxycarbonyl such as lower alkoxycarbonyl (e.g. methoxycarbonyl, ethoxycarbonyl, propoxycarbonyl, butoxycarbonyl, t-butoxycarbonyl, etc.), alkenyloxycarbonyl such as lower alkenyloxycarbonyl (e.g. vinyloxycarbonyl, allyloxycarbonyl, etc.), alkenoyl such as lower alkenoyl (e.g. acryloyl, methacryloyl, crotonoyl, etc.), cycloalkanecarbonyl such as cyclo(lower)alkanecarbonyl (e.g. cyclopropanecarbonyl, cyclopentanecarbonyl, cyclohexanecarbonyl, etc.), and the like.

The aliphatic acyl substituted with aromatic group(s) may include ar(lower)alkoxycarbonyl such as phenyl(lower)alkoxycarbonyl (e.g. benzyloxycarbonyl, phenethyloxycarbonyl, etc.), and the like.

These acyl groups may be further substituted with one or more suitable substituent(s) such as nitro, and the like, and preferable acyl having such substituent(s) may be nitroar(lower)alkoxycarbonyl (e.g. nitrobenzyloxycarbonyl, etc.), and the like.

Preferable example of "imino-protective group" thus defined may be lower alkenyloxycarbonyl and phenyl(or nitrophenyl)(lower)alkoxycarbonyl, more preferable one may be ($C_1$-$C_4$)alkenyloxycarbonyl and phenyl(or nitrophenyl)($C_1$-$C_4$)alkoxycarbonyl.

Suitable "lower alkylene" may include straight or branched one such as methylene, ethylene, trimethylene, tetramethylene, pentamethylene, hexamethylene, methylmethylene, ethylethylene, propylene, and the like, in which more preferable example may be $C_1$-$C_4$ alkenylene.

Suitable imino-protective group in "protected imino" may be the same as those for the "imino-protective group" as mentioned above.

The processes for the preparation of the object compound (I) of the present invention are explained in detail in the following.

Process 1 - ①

The compound (IV) or salts thereof, or the compound (IV) or salts thereof and the compound (V) or salts thereof can be prepared by reacting the compound (II) or salts thereof with the compound (III) or salts thereof. The present reaction is usually carried out in the presence of a Lewis acid and a base.

Suitable Lewis acid may include copper(I) halide (e.g. copper(I) chloride, copper(I) bromide, etc.), cobalt(II) halide (e.g. cobalt(II) chloride, cobalt(II) bromide, etc.), zinc halide (e.g. zinc chloride, zinc bromide, zinc iodide, etc.), halotitanium tri(lower)alkoxide (e.g. chlorotitanium triethoxide, bromotitanium triethoxide, chlorotitanium triisopropoxide, bromotitanium triisopropoxide, etc.), titanium tetrahalide (e.g. titanium tetrachloride, etc.), tin(II) alkanesulfonate (e.g. tin(II) methanesulfonate, tin(II) ethanesulfonate, etc.), tin(II) mono(or di or tri)halo(lower)alkanesulfonate (e.g. tin-(II) trifluoromethanesulfonate, etc.), [mono(or di or tri)halo(lower)alkylsulfonyloxy]tri(lower)alkylsilane [e.g. (trifluoromethylsulfonyloxy)trimethylsilane, (trifluoromethylsulfonyloxy)triethylsilane, etc.], and the like.

Suitable base may include an organic or inorganic base such as alkali metal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), and alkaline earth metal carbonate (e.g. magnesium carbonate, calcium carbonate, etc.), an alkali metal bicarbonate (e.g. sodium bicarbonate, potassium bicarbonate, etc.), lower alkyl alkali metal (e.g. butyllithium, t-butyllithium, etc.), alkali metal di(lower)alkylamide (e.g. lithium dimethylamide, lithium diethylamide, lithium diisopropylamide, etc.), di(lower)alkylamine (e.g. dimethylamine, diethylamine, diisopropylamine, dibutylamine, etc.), tri(lower)alkylamine (e.g. trimethylamine, triethylamine, N,N-diisopropyl-N-ethylamine, etc.), pyridine compound [e.g. pyridine, picoline, lutidine, N,N-di(lower)alkylaminopyridine such as N,N-dimethylaminopyridine, etc.], quinoline, N-lower alkylmorpholine (e.g. N-methylmorpholine, etc.), N,N-di(lower)alkylbenzylamine (e.g. N,N-dimethylbenzylamine, etc.) or the like.

The reaction is usually carried out in a conventional solvent such as acetone, dioxane, acetonitrile, chloroform, methylene chloride, ethylene chloride, tetrahydrofuran, ethyl acetate, N,N-dimethylformamide, dimethyl sulfoxide, benzene, toluene, xylene or any other organic solvent which does not adversely influence the reaction.

The reaction temperature is not critical, and the reaction is usually carried out under from ambient temperature to heating.

Process 1 - ②

The compound (IV) or salts thereof can be prepared by subjecting the compound (V) or salts thereof to rearrangement reaction. The present reaction can be carried out by treating the compound (V) or salts thereof with Lewis acid as mentioned in Process 1 - e,crc/1/ .

The reaction is usually carried out in a conventional solvent such as acetone, dioxane, acetonitrile, chloroform, methylene chloride, ethylene chloride, tetrahydrofuran, ethyl acetate, N,N-dimethylformamide, dimethyl sulfoxide, benzene, toluene, xylene or any other organic solvent which does not adversely influence the reaction.

The reaction temperature is not critical, and the reaction is usually carried out under from ambient temperature to heating.

In the reaction of Process 1, the object compound (IV) or salts thereof can selectively be obtained in the β-form of the following formula:

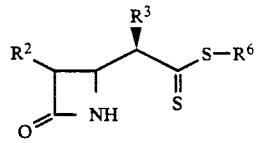

Process 2

The compound (IVb) or salts thereof can be prepared by reacting the compound (IVa) or salts thereof with the compound (XIV) or salts thereof.

The reaction is usually carried out in a conventional solvent such as acetone, dioxane, acetonitrile, chloroform, methylene chloride, ethylene chloride, tetrahydrofuran, ethyl acetate, N,N-dimethylformamide, dimethyl sulfoxide, benzene, toluene, xylene or any other organic solvent which does not adversely influence the reaction.

The reaction temperature is not critical, and the reaction is usually carried out under from cooling to heating.

This reaction is preferably carried out in the presence of a Lewis acid as mentioned in Process 1 - ①.

Process 3 - ①

The compound (VII) or salts thereof can be prepared by reacting the compound (IV) or salts thereof with the compound (VI) or its reactive equivalent or salts thereof.

Suitable reactive equivalent of the compound (VI) may include a compound of the formula:

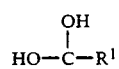

(wherein $R^1$ is as defined above), and the like.

The reaction is usually carried out in a conventional solvent such as acetone, dioxane, acetonitrile, chloroform, methylene chloride, ethylene chloride, tetrahydrofuran, ethyl acetate, N,N-dimethylformamide, dimethyl sulfoxide, benzene, toluene, xylene or any other organic solvent which does not adversely influence the reaction.

The reaction temperature is not critical, and the reaction is usually carried out under from ambient temperature to heating.

Process 3 - ②

The compound (VIII) or salts thereof can be prepared by subjecting the compound (VII) or salts thereof to halogenation reaction. The present halogenation can be carried out by using a conventional halogenating agent such as phosphorus oxyhalide (e.g. phosphorus oxychloride, phosphorus oxybromide, etc.), phosphorus pentahalide (e.g. phosphorus pentabromide, phosphorus pentachloride, phosphorus pentafluoride, etc.), phosphorus trihalide (e.g. phosphorus tribromide, phosphorus trichloride, phosphorus trifluoride, etc.), thionyl halide (e.g. thionyl bromide, thionyl chloride, etc.), a combination of triphenyl phosphine and carbon tetrahalide (e.g. carbon tetrachloride, etc.), or the like.

The reaction is usually carried out in a conventional solvent such as acetone, dioxane, acetonitrile, chloroform, methylene chloride, ethylene chloride, tetrahydrofuran, ethyl acetate, N,N-dimethylformamide, dimethyl sulfoxide, benzene, toluene, xylene or any other organic solvent which does not adversely influence the reaction.

The reaction temperature is not critical, and the reaction is usually carried out under from cooling to heating.

Process 3 - ③

The compound (X) or salts thereof can be prepared by reacting the compound (VIII) or salts thereof with the compound (IX).

The reaction is usually carried out in a conventional solvent such as acetone, dioxane, acetonitrile, chloroform, methylene chloride, ethylene chloride, tetrahydrofuran, ethyl acetate, N,N-dimethylformamide, dimethyl sulfoxide, benzene, toluene, xylene or any other organic solvent which does not adversely influence the reaction.

The reaction temperature is not critical, and the reaction is usually carried out under from cooling to heating.

This reaction is preferably carried out in the presence of an organic or inorganic base such as those given in the explanation of Process 1 - ①.

Process 4 - ①

The compound (XII) or salts thereof can be prepared by reacting the compound (IV) or salts thereof with the compound (XI) or salts thereof.

The reaction is usually carried-out in the presence of a base as mentioned in Process 1 - ①.

The reaction is usually carried out in a conventional solvent such as acetone, dioxane, acetonitrile, chloroform, methylene chloride, ethylene chloride, tetrahydrofuran, ethyl acetate, N,N-dimethylformamide, dimethyl sulfoxide, benzene, toluene, xylene or any other organic solvent which does not adversely influence the reaction.

The reaction temperature is not critical, and the reaction is usually carried out under from cooling to warming.

Process 4 - ②

The compound (X) or salts thereof can be prepared by reacting the compound (XII) or salts thereof with the compound (IX).

The reaction is usually carried out in a conventional solvent such as acetone, dioxane, acetonitrile, chloroform, methylene chloride, ethylene chloride, tetrahydrofuran, ethyl acetate, N,N-dimethylformamide, dimethyl sulfoxide, benzene, toluene, xylene or any other organic solvent which does not adversely influence the reaction.

The reaction temperature is not critical, and the reaction is usually carried out under from warming to heating.

Process 5

The compound (I) or salts thereof can be prepared by subjecting the compound (X) or salts thereof to cyclization reaction.

The reaction is usually carried out in a conventional solvent such as acetone, dioxane, acetonitrile, chloroform, methylene chloride, ethylene chloride, tetrahydrofuran, ethyl acetate, N,N-dimethylformamide, dimethyl sulfoxide, benzene, toluene, xylene or any other organic solvent which does not adversely influence the reaction.

The reaction temperature is not critical, and the reaction is usually carried out under from warming to heating.

Process 6 - ①

The compound (XIII) or salts thereof can be prepared by subjecting the compound (Ia) or salts thereof to oxidation reaction.

The present oxidation can be carried out by a conventional method, for example, by using a oxidizing agent such as an inorganic peracid or a salt thereof (e.g. periodic acid, persulfuric acid, or sodium or potassium salt thereof, etc.), an organic peracid or a salt thereof (e.g. perbenzoic acid, m-chloroperbenzoic acid, performic acid, peracetic acid, chloroperacetic acid, trifluoroperacetic acid, or sodium or potassium salt thereof, etc.), ozone, hydrogen peroxide, peroxoborate (e.g. sodium peroxoborate, etc.), chlorite (e.g. sodium chlorite, etc.), bromite (e.g. sodium bromite, etc.), or the like.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, dimethyl sulfoxide, benzene, toluene, xylene or any other organic solvent which does not adversely influence the reaction.

The reaction temperature is not critical, and the reaction is usually carried out under from cooling to heating.

Process 6 - ②

The compound (Ib) or salts thereof can be prepared by reacting the compound (XIII) or salts thereof with the compound (XIV) or salts thereof.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, dimethyl sulfoxide, benzene, toluene, xylene or any other organic solvent which does not adversely influence the reaction.

The reaction temperature is not critical, and the reaction is usually carried out under from cooling to heating.

The reaction is usually carried out in the presence of a base as mentioned in Process 1 - ①.

Process 7

The compound (Id) or salts thereof can be prepared by subjecting the compound (Ic) or salts thereof to removal reaction of the hydroxy-protective group on $R_a^2$.

This reaction is usually carried out by a conventional method such as hydrolysis, reduction, and the like.

(i) Hydrolysis

Hydrolysis is preferably carried out in the presence of a base or an acid. Suitable base may include an alkali-metal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), and alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using trifluoroacetic acid is usually accelerated by addition of cation trapping agent (e.g. phenol, anisole, etc.).

In case that the hydroxy-protective group is tri(-lower)alkylsilyl, the hydrolysis can be carried out in the presence of tri(lower)alkylammonium halide (e.g. tributylammonium fluoride, etc.).

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base or acid can be also used as the solvent.

The reaction temperature is not critical and the reaction is usually carried out under from cooling to heating.

(ii) Reduction

The reduction method applicable for this removal reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts (e.g. reduced nickel, nickel oxide, Raney nickel, etc.), platinum catalysts (e.g. platinum plate, spongy platinum, platinum black, colloidal, platinum, platinum oxide, platinum wire, etc.), and the like.

In case that the catalytic reduction is applied, the reaction is preferably carried out around neutral condition.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from cooling to warming.

Suitable salts of the compounds in the above Processes can be referred to the ones as exemplified for the compound (I).

The following Preparations and Examples are given for the purpose of illustrating this invention in more detail.

PREPARATION 1

15% Aqueous sodium methanethiolate (250 g) was added to a mixture of water (250 ml) and tetrahydrofuran (150 ml) and the solution was cooled at 0°-5° C. Benzyltrimethylammonium chloride (0.10 g) was added and a solution of propionyl chloride (46.5 ml) in tetrahydrofuran (47 ml) was dropwise added with stirring in the period of 1.5 hours. The mixture was then stirred at 0°-5° C. for 30 minutes and at room temperature for 1 hour. The mixture was extracted with isopropyl ether (200 ml). The organic phase was washed with water (200 ml×2), dried over magnesium sulfate and the filtrate was distilled under 760 mmHg to remove tetrahydrofuran and isopropyl ether. The residual oil was distilled at 64°-70° C. under 135 mmHg to give S-methyl propanethioate (37.8 g).

NMR (CDCl$_3$, $\delta$): 1.19 (3H, t), 2.30 (3H, s), 2.58 (2H, q)

PREPARATION 2

A mixture of S-methyl propanethioate (12.0 g) and phosphorus pentasulfide (8.47 g) was stirred at 90° C. for 10.5 hours. After cooling down to room temperature, 5% sodium bicarbonate (100 ml) and methylene chloride (50 ml) were added to the mixture and the mixture was stirred for 30 minutes. The separated methylene chloride layer was washed with water (30 ml×2), dried over magnesium sulfate and evaporated at 20° C. under 160 mmHg. The residual oil was distilled at 48°-50° C. under 16 mmHg to give methyl propanedithioate (7.02 g).

NMR (CDCl$_3$, $\delta$): 1.37 (3H, t), 2.62 (3H, s), 3.05 (2H, q)

PREPARATION 3

To a suspension of sodium hydride (60% in oil, 2.0 g) in anhydrous tetrahydrofuran (50 ml) was added propanedithioic acid (5.0 g) with ice-cooling. A solution of (2S,4R)-1-allyloxycarbonyl-2-(2-fluoroethyloxymethyl)-4-methylsulfonyloxypyrrolidine (16.25 g) in anhydrous tetrahydrofuran (50 ml) was added dropwise to the mixture and the mixture was heated at 60°-70° C. for 4 hours. The solution was poured into ice-water (100 ml) and extracted with diethyl ether. The organic layer was washed with 1N aqueous sodium hydroxide solution (50 ml) and brine, dried, and evaporated under reduced pressure. The residue was purified by column chromatography on silica gel [n-hexane-ethyl acetate (10:1, V/V)] to afford (2S,4S)-1-allyloxycarbonyl-2-(2-fluoroethyloxymethyl)-4-[(1-thioxopropyl)thio]pyrrolidine (9.47 g).

IR (Neat): 1700 cm$^{-1}$

NMR (CDCl$_3$, $\delta$): 1.35 (3H, t, J=7.4 Hz), 2.07-2.19 (1H, m), 2.50-2.66 (1H, m), 2.99 (2H, q, J=7.4 Hz), 3.28 (1H, dd, J=11 and 6.1 Hz), 3.62-3.81 (4H, m), 4.10-4.44 (4H, m), 4.58-4.72 (3H, m), 5.19-5.35 (2H, m), 5.84-6.00 (1H, m)

EXAMPLE 1

(1) To a suspension of anhydrous zinc chloride (45.3 g) in acetonitrile (450 ml) cooled to 0° C. was added triethylamine (101 g). After stirring for 30 minutes at 0° C., the solution was cooled to −35° C. and a mixture of methyl dithiopropionate (20.0 g) and (3R,4R)-4-acetoxy-3-[(1R)-1-(tert-butyldimethylsilyloxy)ethyl]-2-oxoazetidine (23.9 g) in acetonitrile (90 ml) was added thereto. The reaction mixture was stirred at −20° C. for 2 hours, warmed to 0° C., and additionally stirred for 30 minutes at 0° C. The mixture was poured into a stirred mixture of dichloromethane (800 ml) and 1N hydrochloric acid (1000 ml). The organic layer was separated, washed with water, aqueous sodium bicarbonate solution and brine, and dried. The solution was concentrated under reduced pressure and the solid residue was washed with n-hexane to afford (3S,4S)-3-[(1R)-1-(tert-butyldimethylsilyloxy)ethyl]-4-[(1R)-1-{(methylthio)-thiocarbonyl}ethyl]-2-oxoazetidine (20.1 g) as a yellow crystal.

The same compound was also obtained by using cobalt(II) chloride instead of zinc chloride.

mp: 147°-148° C.

IR (Nujol): 3150, 3075, 1758 cm$^{-1}$

NMR (CDCl$_3$, δ): 0.06 (6H, s), 0.87 (9H, s), 1.10 (3H, d, J=6.3 Hz), 1.38 (3H, d, J=6.7 Hz), 2.62 (3H, s), 2.93-2.96 (1H, m), 3.44-3.58 (1H, m), 3.89 (1H, dd, J=2.2 and 5.6 Hz), 4.12-4.21 (1H, m), 6.00 (1H, br s)

The following compounds were obtained according to a similar manner to that of Example 1(1).

(2) (3S,4S)-3-[(1R)-1-(tert-Butyldimethylsilyloxy)ethyl]-4-[(1R)-1-{(phenylthio)thiocarbonyl}ethyl]-2-oxoazetidine NMR (CDCl$_3$, δ): 0.07 (3H, s), 0.08 (3H, s), 0.89 (9H, s), 1.19 (3H, d, J=6.3 Hz), 1.42 (3H, d, J=6.8 Hz), 3.01 (1H, m), 3.62-3.68 (1H, m), 3.97 (1H, dd, J=5.5 and 2.2 Hz), 4.14-4.25 (1H, m), 6.04 (1H, br s), 7.34-7.39 (2H, m), 7.48-7.51 (3H, m)

(3) (3S,4S)-3-[(1R)-1-(tert-Butyldimethylsilyloxy)ethyl]-4-[(1R)-1-{(ethylthio)thiocarbonyl}ethyl]-2-oxoazetidine IR (Nujol): 1712, 1761 cm$^{-1}$ NMR (CDCl$_3$, δ): 0.05 (6H, s), 0.87 (9H, s), 1.12 (3H, d, J=6.3 Hz), 1.28-1.38 (6H, m), 2.92-2.97 (1H, m), 3.21 (2H, q, J=7.4 Hz), 3.42-3.48 (1H, m), 3.88-3.92 (1H, dd, J=5.6 and 2.1 Hz), 4.10-4.22 (1H, m), 5.99 (1H, br s)

(4) (3S,4S)-4-[(1R)-1-{(Benzylthio)thiocarbonyl}ethyl]-3-[(1R)-1-(tert-butyldimethylsilyloxy)ethyl]-2-oxoazetidine IR (Nujol): 1710, 1750 cm$^{-1}$ NMR (CDCl$_3$, δ): 0.05 (6H, s), 0.86 (9H, s), 1.06 (3H, d, J=6.4 Hz), 1.38 (3H, d, J=6.8 Hz), 2.93 (1H, m), 3.43-3.49 (1H, m), 3.91 (1H, dd, J=5.6 and 2.2 Hz), 4.11-4.17 (1H, m), 4.44 (2H, s), 6.00 (1H, br s), 7.30 (5H, s)

EXAMPLE 2

To a solution of diisopropylamine (152 mg) in anhydrous tetrahydrofuran (2 ml) cooled to 0° C. was added a 1.56M solution of n-butyllithium in n-hexane (0.95 ml). After stirring for 30 minutes at 0° C., the solution was cooled to −78° C. and methyl dithiopropionate (120 mg) and a 1M solution of chlorotitanium triisopropoxide in hexane (4.0 ml) were added successively thereto. The mixture was warmed to −40° C. and (3R,4R)-4-acetoxy-3-[(1R)-1-(tert-butyldimethylsilyloxy)ethyl]-2-oxoazetidine (287 mg) was added thereto. The solution was allowed to warm to 0° C., quenched by 1N hydrochroric acid, and extracted with diethyl ether. The organic layer was washed with brine, dried, and concentrated under reduced pressure. The residue was purified by flash chromatography on silica gel (10% diethyl ether-hexane) to afford a mixture (202 mg) of (3S,4S)-3-[(1R)-1-(tert-butyldimethylsilyloxy)ethyl]-4-[(1R)-1-[(methylthio)thiocarbonyl}ethyl]-2-oxoazetidine and (3S,4S)-3-[(1R)-1-(tert-butyldimethylsilyloxy)ethyl]-4-[(1S)-1-{(methylthio)thiocarbonyl}ethyl]-2-oxoazetidine. Recrystallization of the product obtained above from n-hexane gave (3S,4S)-3-[(1R)-1-(tert-butyldimethylsilyloxy)ethyl]-4-[(1R)-1-{(methylthio)thiocarbonyl}ethyl]-2-oxoazetidine as a yellow needle.

NMR (CDCl$_3$, δ): 0.06 (6H, s), 0.87 (9H, s), 1.10 (3H, d, J=6.3 Hz), 1.38 (3H, d, J=6.7 Hz), 2.62 (3H, s), 2.93-2.96 (1H, m), 3.44-3.58 (1H, m), 3.89 (1H, dd, J=2.2 and 5.6 Hz), 4.12-4.21 (1H, m), 6.0 (1H, br s)

EXAMPLE 3

To a suspension of Tin(II) trifluoromethanesulfonate (5.58 g) in dichloromethane (27 ml) cooled to −25° C. were added triethylamine (1.62 g) and methyl dithiopropionate (1.20 g) successively. The mixture was stirred for 2 hours at −20° C. and (3R,4R)-4-acetoxy-3-[(1R)-1-(tertbutyldimethylsilyloxy)ethyl]-2-oxoazetidine (2.0 g) was added thereto. After stirring for 2 hours at 0° C., the mixture was poured into 20% aqueous solution of oxalic acid (100 ml) and the precipitates were filtered off. The organic layer of the filtrate was separated, dried, and concentrated under reduced pressure. The residue was purified by silica gel (50 g) column chromatography (20% ethyl acetate-hexane) to afford (3S,4R)-3-[(1R)-1-(tertbutyldimethylsilyloxy)ethyl]-4-[(1-methylthio-1-propenyl)thio]-2-oxoazetidine (mixture of E and Z isomers) (1.14 g).

IR (Nujol): 3150, 1760, 1720 cm$^{-1}$

NMR (CDCl$_3$, δ): 0.07 (3H, s), 0.08 (3H, s), 0.88 (9H, s), 1.23 (0.45H, d, J=6.3 Hz), 1.25 (2.55H, d, J=6.3 Hz), 1.92 (3H, d, J=6.8 Hz), 2.31 (3H, s), 3.14-3.17 (0.15H, m), 3.17-3.21 (0.85H, m), 4.19-4.31 (1H, m), 5.00 (0.15H, d, J=2.5 Hz), 5.02 (0.85H, d, J=2.5 Hz), 6.08 (0.85H, q, J=6.8 Hz), 6.23 (1H, br s), 6.32 (0.15H, q, J=6.8 Hz)

Further elution of the column gave a mixture (1.01 g) of (3S,4S)-3-[(1R)-1-(tert-butyldimethylsilyloxy)ethyl]-4-[(1R)-1-{(methylthio)thiocarbonyl}ethyl]-2-oxoazetidine and (3S,4S)-3-[(1R)-1-(tert-butyldimethylsilyloxy)ethyl]-4-[(1S)-1-{(methylthio)thiocarbonyl}ethyl]-2-oxoazetidine.

NMR (CDCl$_3$, δ): 0.06 (6H), 0.87 (6H, s), 0.88 (3H, s), 1.10 (2H, d, J=6.3 Hz), 1.27 (1H, d, J=6.3 Hz), 1.38 (3H, d, J=6.7 Hz), 2.62 (2H, s), 2.65 (1H, s), 2.82-2.86 (0.33H, m), 2.93-2.96 (0.67H, m), 3.31-3.41 (0.33H, m), 3.45-3.58 (0.67H, m), 3.89 (0.67H, dd, J=2.2 and 5.7 Hz), 3.98 (0.33H, dd, J=2.0 and 9.5 Hz), 4.09-4.21 (1H, m), 5.82 (0.33H, br s), 6.04 (0.67H, br s)

EXAMPLE 4

To a solution of (2S,4S)-1-allyloxycarbonyl-2-(2-fluoroethyloxymethyl)-4-[(1-thioxopropyl)thio]pyrrolidine (325 mg) in anhydrous tetrahydrofuran (5 ml) cooled to 0° C. was added sodium hydride (60% in oil, 40 mg). After ceasing of gas evolution, zinc bromide (1.0 g) in tetrahydrofuran was added to the mixture and the mixture was stirred for 1 hour at 0° C. and additional 1 hour at the ambient temperature. The reaction mixture was quenched by water and extracted with diethyl ether. The organic layer was washed with brine, dried, and concentrated under reduced pressure. The residue was purified by column chromatography on silica gel [diethyl ether-n-hexane (1:5, V/V)] to give (3S,4R)-4-[1-{(2S,4S)-1-allyloxycarbonyl-2-(2-fluoroethyloxymethyl)pyrrolidin-4-ylthio}-1-propenyl]thio-3-[(1R)-1-(tert-butyldimethylsilyloxy)ethyl]-2-oxoazetidine (mixture of E and Z isomers) (188 mg).

NMR (CDCl$_3$, δ): 0.07 and 0.08 (6H, each s), 0.89 and 0.88 (9H, each s), 1.22 and 1.24 (3H, each d, J=6.3 Hz), 1.92 and 1.94 (3H, each d, J=6.8 Hz), 1.96-2.10 (1H, m), 2.38-2.53 (1H, m), 3.15-3.29 (2H, m), 3.61-3.81 (4H, m), 4.00-4.17 (1H, m), 4.20-4.28 (1H, m), 4.42 (1H, dd, J=4.1 Hz), 4.58-4.68 (3H, m), 5.02 (1H, br s), 5.03-5.34 (2H, m), 5.84-6.04 (1H, m), 6.30 and 6.33 (1H, each br s), 6.36-6.50 (1H, m)

Further elution of the column [diethyl ether-n-hexane (1:1, V/V)] gave a crude mixture of (3S,4S)-4-[(1R)-1-{((2S,4S)-1-allyloxycarbonyl-2-(2-fluoroethoxymethyl)pyrrolidin-4-ylthio)thiocarbonyl}ethyl]-3-[(1R)-1-(tert-butyldimethylsilyloxy)ethyl]-2-oxoazetidine and (3S,4S)-4-[(1S)-1-{((2S,4S)-1-allyloxycarbonyl-2-(2-fluoroethoxymethyl)pyrrolidin-4-ylthio)thiocarbonyl}ethyl]-3-[(1R)-1-(tert-butyldimethylsilyloxy)ethyl]-2-oxoazetidine, which was purified by preparative thin layer chromatography.

NMR (CDCl$_3$, $\delta$): 0.07 and 0.08 (6H, each s), 0.87 and 0.88 (9H, each s), 1.12 and 1.27 (3H, each d, J=6.3 and 6.1 Hz), 1.36 (3H, d, J=6.7 Hz), 2.04–2.15 (1H, m), 2.52–2.72 (1H, m), 2.80–2.83 and 2.93–2.96 (1H, m), 3.23–3.32 and 3.41–3.51 (2H, m), 3.62–3.81 (4H, m), 3.88–3.98 (1H, m), 4.14–4.30 (4H, m), 4.42 (1H, dd, J=4.1 Hz), 4.58–4.68 (3H, m), 5.20–5.35 (2H, m), 5.35–6.00 (2H, m)

EXAMPLE 5

A mixture of (3S,4R)-3-[(1R)-1-(tert-butyldimethylsilyloxy)ethyl]-4-[(1-methylthio-1-propenyl)thio]-2-oxoazetidine (mixture of E and Z isomers) (0.60 g) and anhydrous zinc chloride (1.36 g) in anhydrous tetrahydrofuran was heated under reflux for 2 hours. The mixture was quenched by 1N hydrochrolic acid and extracted with ethyl acetate. The organic layer was washed with saturated sodium bicarbonate solution, brine, dried, and concentrated under reduced pressure. The residue was purified by silica gel (25 g) column chromatography (33% ethyl acetate-hexane) to afford a mixture (2:1)(0.344 g) of (3S,4S)-3-[(1R)-1-(tert-butyldimethylsilyloxy)ethyl]-4-[(1R)-1-{(methylthio)thiocarbonyl}ethyl]-2-oxoazetidine and (3S,4S)-3-[(1R)-1-(tert-butyldimethylsilyloxy)ethyl]-4-[(1S)-1-{(methylthio)thiocarbonyl}ethyl]-2-oxoazetidine.

EXAMPLE 6

(1) To a solution of (3S,4S)-3-[(1R)-1-(tertbutyldimethylsilyloxy)ethyl]-4-[(1R)-1-{(methylthio)thiocarbonyl}ethyl]-2-oxoazetidine (700 mg) in toluene (7 ml) was added allyl dihydroxyacetate (560 mg), and the mixture was heated under reflux for 3 hours. The solution was washed with water, dried, and evaporated under reduced pressure to give a mixture (903 mg) of (3S,4S)-1-[(1R)-1-(allyloxycarbonyl)-1-hydroxymethyl]-3-[(1R)-1-(tert-butyldimethylsilyloxy)ethyl]-4-[(1R)-1-{(methylthio)thiocarbonyl}ethyl]-2-oxoazetidine and (3S,4S)-1-[(1S)-1-(allyloxycarbonyl)-1-hydroxymethyl]-3[(1R)-1-(tert-butyldimethylsilyloxy)ethyl]-4-[(1R)-1-{(methylthio)thiocarbonyl}ethyl]-2-oxoazetidine.

IR (Neat): 3100–3500 (br), 1740–1765 (br) cm$^{-1}$

NMR (CDCl$_3$, $\delta$): 0.04–0.06 (6H), 0.87–0.89 (9H), 1.12 and 1.17 (3H, each d), 1.46 and 1.47 (3H, each d), 2.62 and 2.63 (3H, each s), 3.03–3.12 (1H, m), 3.23–3.37 (1H, m), 4.05–4.19 (2H, m), 5.23–5.49 (3H, m), 5.83–6.04 (2H, m)

The following compound was obtained according to a similar manner to that of Example 6(1).

(2) Mixture of (3S,4S)-1-[(1R)-1-(allyloxycarbonyl)-1-hydroxymethyl]-3-[(1R)-1-(tert-butyldimethylsilyloxy)ethyl]-4-[(1R)-1-{(benzylthio)thiocarbonyl}ethyl]-2-oxoazetidine and (3S,4S)-1-[(1S)-1-(allyloxycarbonyl)-1-hydroxymethyl]-3-[(1R)-1-(tert-butyldimethylsilyloxy)ethyl]-4-[(1R)-1-{(benzylthio)thiocarbonyl}ethyl]-2-oxoazetidine.

IR (Neat): 3100–3600 (br), 1750 (br) cm$^{-1}$

EXAMPLE 7

To a mixture of dichloromethane (32.6 mg) and a mixture (33.1 mg) of (3S,4S)-3-[(1R)-1-(tertbutyldimethylsilyloxy)ethyl]-4-[(1R)-1-{(methylthio)thiocarbonyl}ethyl]-2-oxoazetidine and (3S,4S)-3-[(1R)-1-(tert-butyldimethylsilyloxy)ethyl]-4-[(1S)-1-{(methylthio)thiocarbonyl}ethyl]-2-oxoazetidine were added triethylamine (30.4 mg) and allyl chloroglyoxylate (32.6 mg) successively at 0° C. After stirring for 10 minutes at the same temperature, the solution was washed with water, 1N hydrochloric acid, brine, and dried. The solvent was removed under reduced pressure and the residue was purified by flash chromatography (5% diethyl ether-hexane) to afford a mixture (23 mg) of (3S,4S)-1-(allyloxyoxalyl)-3-[(1R)-1-(tert-butyldimethylsilyloxy)ethyl]-4-[(1R)-1-{(methylthio)thiocarbonyl}ethyl]-2-oxoazetidine and (3S,4S)-1-(allyloxyoxalyl)-3-[(1R)-1-(tert-butyldimethylsilyloxy)ethyl]-4-[1S)-1-{(methylthio)thiocarbonyl}ethyl]-2-oxoazetidine.

IR (Neat): 1805, 1750, 1700 cm$^{-1}$

NMR (CDCl$_3$, $\delta$): 0.16 (3H, s), 0.67 (3H, s), 0.83 (9H, s), 1.01 (2H, d, J=6.3 Hz), 1.12 (1H, d, J=6.3 Hz), 1.38 (2H, d, J=6.8 Hz), 1.47 (1H, d, J=6.8 Hz), 2.61 (1H, s), 2.63 (2H, s), 3.38 (0.67H, t, J=3 Hz), 3.72 (0.33H, t, J=2.9 Hz), 4.09 (1H, m), 4.25–4.31 (1H, m), 4.56 (0.33H, dd, J=3.1 and 6.4 Hz), 4.65 (0.67H, dd, J=3.2 and 5.6 Hz), 4.76–4.81 (2H, m), 5.28–5.47 (2H, m), 5.87–6.05 (1H, m)

EXAMPLE 8

The following compounds were obtained according to a similar manner to that of Example 7.

(1) Mixture of (3S,4S)-1-(allyloxyoxalyl)-4-[(1R)-1-{((2S,4S)-1-allyloxycarbonyl-2-(2-fluoroethyloxymethyl)pyrrolidin-4-ylthio)thiocarbonyl}ethyl]-3-[(1R)-1-(tert-butyldimethylsilyloxy)ethyl]-2-oxoazetidine and (3S,4S)-1-(allyloxyoxalyl)-4-[(1S)-1-{((2S,4S)-1-allyloxycarbonyl-2-fluoroethyloxymethyl)pyrrolidin-4-ylthio)thiocarbonyl}ethyl]-3-[(1R)-1-(tertbutyldimethylsilyloxy)ethyl]-2-oxoazetidine IR (Neat): 1805, 1750, 1700 cm$^{-1}$ NMR (CDCl$_3$, $\delta$): 0.05 (6H, s), 0.83 (9H, s), 1.04–1.45 (6H, m), 2.00–2.22 (1H, m), 2.51–2.75 (1H, m), 3.04–3.37 (2H, m), 3.60–3.81 (4H, m), 3.93–4.35 (4H, m), 4.39–4.43 (1H, m), 4.58–4.68 (4H, m), 4.76–4.80 (3H, m), 5.19–5.44 (4H, m), 5.86–6.00 (2H, m)

(2) (3S,4S)-1-(Allyloxyoxalyl)-4-[(1R)-1-{(benzylthio)thiocarbonyl}ethyl]-3-[(1R)-1-(tert-butyldimethylsilyloxy)ethyl}-2-oxoazetidine IR (Nujol): 1690, 1735, 1795 cm$^{-1}$ NMR (CDCl$_3$, $\delta$): 0.05 (6H, s), 0.84 (9H, s), 1.09 (3H, d, J=6.4 Hz), 1.48 (3H, d, J=6.6 Hz), 3.70 (1H, t, J=3.0 Hz), 3.98–4.15 (1H, m), 4.24–4.28 (1H, m), 4.43 (2H, s), 4.55–4.60 (1H, m), 4.78 (2H, d, J=6.0 Hz), 5.28–5.44 (2H, m), 5.85–6.05 (1H, m), 7.30 (5H, s)

EXAMPLE 9

(1) To a mixture of 2,6-lutidine (64 mg), ethyl acetate (1 ml) and a mixture (50 mg) of (3S,4S)-1-[(1R)-1-(allyloxycarbonyl)-1-hydroxymethyl]-3-[(1R)-1-(tert-butyldimethylsilyloxy)ethyl] -4-[(1R)-1-{(methylthio)thiocarbonyl}ethyl]-2-oxoazetidine and (3S,4S)-1-[(1S)-1-(allyloxycarbonyl)-1-hydroxymethyl]-3-[(1S)-1-(tert-butyldimethylsilyloxy)ethyl]-4-[(1R)-1-{(methylthio)thiocarbonyl}ethyl]-2-oxoazetidine was added a 1M solution of thionyl chloride in ethyl acetate (0.3 ml) with ice-bath cooling, and the mixture was stirred for 5 minutes at the same temperature. Hexane (2 ml) was added to the mixture and the mixture was filtered. The filtrate was concentrated under reduced pressure and the residue was dissolved in N,N-dimethylformamide (0.5 ml). To this solution were added triphenylphosphine (44 mg) and 2,6-lutidine (20 mg) and the mixture was allowed to stand at the ambient temperature for 17 hours. Hexane (6 ml) and water (3 ml) were added and the organic layer was washed with water, dried, and evaporated under reduced pressure. The residue was purified by preparative thin layer chromatography [hexane-ethyl acetate (1:1, V/V)] to afford (3S,4S)-1-[1-(allyloxycarbonyl)-1-(triphenylphosphoranediyl)methyl]-3-[(1R)-1-(tertbutyldimethylsilyloxy)ethyl]-4-[(1R)-1-{(methylthio)thiocarbonyl}ethyl]-2-oxoazetidine (28.7 mg).

IR (Nujol): 1740 cm$^{-1}$

The following compound was obtained according to a similar manner to that of Example 9(1).

(2) (3S,4S)-1-[1-(Allyloxycarbonyl)-1-(triphenylphosphoranediyl)methyl]-4-[(1R)-1-{(benzylthio)thiocarbonyl}ethyl]-3-[(1R)-1-(tert-butyldimethylsilyloxy)ethyl]-2-oxoazetidine IR (CHCl$_3$): 1725 cm$^{-1}$ NMR (CDCl$_3$, δ): 0.08 (6H, s), 0.88 (9H, s)

EXAMPLE 10

(1) A mixture of triethyl phosphite (1.43 g), toluene (3 ml) and a mixture (1.0 g) of (3S,4S)-1-(allyloxyoxalyl)-3-[(1R)-1-(tert-butyldimethylsilyloxy)ethyl]-4-[(1R)-1-{(methylthio)thiocarbonyl}ethyl]-2-oxoazetidine and (3S,4S)-1-(allyloxyoxalyl)-3-[(1R)-1-(tert-butyldimethylsilyloxy)ethyl]-4-[(1S)-1-{(methylthio)thiocarbonyl}ethyl]-2-oxoazetidine was heated at 80° C. for 26 hours and then refluxed for 16 hours. After removal of the solvent, the residue was dissolved in hexane, washed with water, dried, and concentrated in vacuo. The oily residue was purified by silica gel column chromatography [diethyl ether-hexane (1:3, V/V)] to afford a mixture (118 mg) of allyl (4R,5S,6S)-6-[(1R)-1-(tert-butyldimethylsilyloxy)ethyl]-4-methyl-3-methylthio-7-oxo-1-azabicyclo[3.2.0]hept-2-ene-2-carboxylate and allyl (4S,5S,6S)-6-[(1R)-1-(tert-butyldimethylsilyloxy)ethyl]-4-methyl-3-methylthio-7-oxo-1-azabicyclo[3.2.0]hept-2-ene-2-carboxylate.

IR (Neat): 1775, 1710 cm$^{-1}$

NMR (CDCl$_3$, δ): 0.08 and 0.09 (6H, each s), 0.88 and 0.89 (9H, each s), 1.23 and 1.39 (3H, each d), 1.26 (3H, d), 2.26 and 2.39 (3H, each s), 3.14–3.21 (1H, m), 3.28–3.36 (1H, m), 3.69 (0.3H, dd, J=6.9 and 3.0 Hz), 4.14 (0.7H, dd, J=9.2 and 2.5 Hz), 4.16–4.26 (1H, m), 4.71–4.83 (2H, m), 5.21–5.50 (2H, m), 5.87–6.03 (1H, m)

The following compound was obtained according to a similar manner to that of Example 10(1).

(2) Allyl (4R,5S,6S)-3-benzylthio-6-[(1R)-1-(tert-butyldimethylsilyloxy)ethyl]-4-methyl-7-oxo-1-azabicyclo[3.2.0]hept-2-ene-2-carboxylate

EXAMPLE 11

The following compounds were obtained by treating a mixture of (3S,4S)-1-(allyloxyoxalyl)-4-[(1R)-1-{((2S,4S)-1-allyloxycarbonyl-2-(2-fluoroethyloxymethyl)pyrrolidin-4-ylthio)thiocarbonyl}ethyl]-3-[(1R)-1-(tertbutyldimethylsilyloxy)ethyl]-2-oxoazetidine and (3S,4S)-1-(allyloxyoxalyl)-4-[(1S)-1-{((2S,4S)-1-allyloxycarbonyl-2-(2-fluoroethyloxymethyl)pyrrolidin-4-ylthio)thiocarbonyl}ethyl]-3-[(1R)-1-(tertbutyldimethylsilyloxy)ethyl]-2-oxoazetidine according to a similar manner to that of Example 10(1).

Allyl (4R,5S,6S)-3-[(2S,4S)-1-allyloxycarbonyl-2-(2-fluoroethyloxymethyl)pyrrolidin-4-ylthio]-6-[(1R)-1-(tert-butyldimethylsilyloxy)ethyl]-4-methyl-7-oxo-1-azabicyclo[3.2.0]hept-2-ene-2-carboxylate IR (Neat): 1775, 1710 cm$^{-1}$ NMR (CDCl$_3$, δ): 0.86 (6H, s), 0.89 (9H, s), 1.25 (6H, d, J=6.2 Hz), 1.98–2.13 (1H, m), 2.41–2.56 (1H, m), 3.21–3.31 (3H, m), 3.58–3.66 (3H, m), 3.76–3.80 (2H, m), 3.95–4.24 (4H, m), 4.42 (1H, t, J=4.1 Hz), 4.58–4.84 (5H, m), 5.20–5.49 (4H, m), 5.84–6.05 (2H, m)

Allyl (4S,5S,6S)-3-[(2S,4S)-1-allyloxycarbonyl-2-(2-fluoroethyloxymethyl)pyrrolidin-4-ylthio]-6-[(1R)-1-(tert-butyldimethylsilyloxy)ethyl]-4-methyl-7-oxo-1-azabicyclo[3.2.0]hept-2-ene-2-carboxylate NMR (CDCl$_3$, δ): 0.08 (6H, s), 0.88 (9H, s), 1.26 (3H, d, J=6.1 Hz), 1.36 (3H, d, J=7.0 Hz), 1.90–2.10 (1H, m), 2.12–2.58 (1H, m), 3.11–3.29 (2H, m), 3.58–4.32 (10H, m), 4.41 (1H, t, J=4.1 Hz), 4.57–4.76 (5H, m), 5.20–5.49 (4H, m), 5.84–6.05 (2H, m)

EXAMPLE 12

(1) A solution of (3S,4S)-1-[1-(allyloxycarbonyl)-1-(triphenylphosphoranediyl)methyl]-3-[(1R)-1-(tertbutyldimethylsilyloxy)ethyl]-4-[(1R)-1-{(methylthio)thiocarbonyl}ethyl]-2-oxoazetidine (325 mg) in toluene (3 ml) was heated under reflux for 4.5 hours. The solvent was removed under reduced pressure and the residue was purified by silica gel column chromatography [ethyl acetate-hexane (1:3, V/V)] to afford allyl (4R,5S,6S)-6-[(1R)-1-(tert-butyldimethylsilyloxy)ethyl]-4-methyl-3-methylthio-7-oxo-1-azabicyclo[3.2.0-]hept-2-ene-2-carboxylate (164 mg).

IR (Nujol): 1772, 1695 cm$^{-1}$

NMR (CDCl$_3$, δ): 0.08 (6H, s), 0.88 (9H, s), 1.23 (3H, d, J=6.7 Hz), 1.27 (3H, d, J=5.9 Hz), 2.39 (3H, s), 3.19 (1H, dd, J=6.5 and 2.5 Hz), 3.25–3.40 (1H, m), 4.14 (1H, dd, J=9.2 and 2.5 Hz), 4.16–4.29 (1H, m), 4.63–4.85 (2H, m), 5.20–5.49 (2H, m), 5.86–6.06 (1H, m)

The following compound was obtained according to a similar manner to that of Example 12(1).

(2) Allyl (4R,5S,6S)-3-benzylthio-6-[(1R)-1-(tert-butyldimethylsilyloxy)ethyl]-4-methyl-7-oxo-1-azabicyclo[3.2.0]hept-2-ene-2-carboxylate IR (Neat): 1700, 1765 cm$^{-1}$ NMR (CDCl$_3$, δ): 0.06 (3H, s), 0.07 (3H, s), (0.87 (9H, s), 1.22 (3H, d, J=4.4 Hz), 1.26 (3H, d, J=3.2 Hz), 3.17 (1H, dd, J=6.5 and 2.6 Hz), 3.26–3.34 (1H, m), 4.03–4.07 (3H, m), 4.17–4.23 and 1.3 Hz), 5.44 (1H, dd, J=17.2 and 1.54 Hz), 5.87–6.02 (1H, m), 7.32 (5H, s)

EXAMPLE 13

(1) To a solution of allyl (4R,5S,6S)-6-[(1R)-1-(tertbutyldimethylsilyloxy)ethyl]-4-methyl-3-methylthio-7-oxo-1-azabicyclo[3.2.0]hept-2-ene-2-carboxylate (66 mg) in dichloromethane (1 ml) cooled to 0° C. was added meta-chloroperbenzoic acid (27.7 mg). The mixture was stirred for 10 minutes at the same temperature, washed with aqueous sodium bicarbonate solution and dried. The solvent was removed under reduced pressure and the residue was purified by silica gel chromatography to give allyl (4R,5S,6S)-6-[(1R)-1-(tert-butyldimethylsilyloxy)ethyl]-4-methyl-3-methylsulfinyl-7-oxo-1-azabicyclo[3.2.0]hept-2-ene-2-carboxylate (64 mg).

IR (Neat): 1785, 1710 cm$^{-1}$

NMR (CDCl$_3$, δ): 0.08 (6H, s), 0.88 (9H, s), 1.25 (3H, d, J=6.1 Hz), 1.38 and 1.42 (3H, each d), 2.86 and 2.91 (3H, each s), 3.33–3.40 (1H, m), 3.60–3.86 (1H, m), 4.23–4.70 (2H, m), 4.71–4.77 (2H, m), 5.27–5.52 (2H, m), 5.82–6.03 (1H, m)

The following compound was obtained according to a similar manner to that of Example 13(1).

(2) Allyl (4R,5S,6S)-3-benzylsulfinyl-6-[(1R)-1-(tert-butyldimethylsilyloxy)ethyl]-4-methyl-7-oxo-1-azabicyclo[3.2.0]hept-2-ene-2-carboxylate IR (CHCl$_3$): 1705, 1770 cm$^{-1}$ NMR (CDCl$_3$, δ): 0.86 (9H, s), 2.48–2.56 (1H, m), 3.15 (1H, dd, J=6.2 and 2.8 Hz), 3.77 (1H, dd, J=9.4 and 2.7 Hz), 4.77–4.79 (2H, m), 5.88–6.05 (1H, m)

EXAMPLE 14

To a solution of allyl (4R,5S,6S)-6-[(1R)-1-(tertbutyldimethylsilyloxy)ethyl] -4-methyl-3-methylthio-7-oxo-1-azabicyclo[3.2.0]hept-2-ene-2-carboxylate (31.4 mg) in a mixture of acetone (1.0 ml) and ethanol (0.1 ml) was added a 30% aqueous solution of hydrogen peroxide (0.2 ml). The reaction was allowed to stand at ambient temperature for 4 days. The mixture was diluted with ethyl acetate, washed with water, 5% aqueous sodium thiosulfate solution, brine, and dried. The solvent was removed off under reduced pressure and the residue was purified by silica gel column chromatography [ethyl acetate-n-hexane (1:3, V/V)] to afford allyl (4R,5S,6S)-6-[(1R)-1-(tert-butyldimethylsilyloxy)ethyl]-4-methyl-3-methylsulfinyl-7-oxo-1-azabicyclo[3.2.0]hept-2-ene-2-carboxylate (10.1 mg).

EXAMPLE 15

To a mixture of allyl (4R,5S,6S)-6-[(1R)-1-(tertbutyldimethylsilyloxy)ethyl]-4-methyl-3-methylsulfinyl-7-oxo-1-azabicyclo[3.2.0]hept-2-ene-2-carboxylate (33 mg) and (2S,4S)-1-allyloxycarbonyl-2-(2-fluoroethyloxymethyl)-4-mercaptopyrrolidine (21 mg) in N,N-dimethylformamide (1.0 ml) was added diisopropylethylamine (10 mg). After stirring for 2 hours at ambient temperature, the solution was diluted with diethyl ether (10 ml) and washed with water, 1N hydrochloric acid, aqueous sodium bicarbonate solution and brine, dried, and evaporated under reduced pressure. The residue was purified by preparative thin layer chromatography [ethyl acetate-n-hexane (1:1.5, V/V)] to give allyl (4R,5S,6S)-3-[(2S,4S)-1-allyloxycarbonyl-2-(2-fluoroethyloxymethyl)pyrrolidin-4-ylthio]-6-[(1R)-1-(tert-butyldimethylsilyloxy)ethyl]-4-methyl-7-oxo-1-azabicyclo[3.2.0]hept-2-ene-2-carboxylate (21 mg).

IR (Neat): 1775, 1710 cm$^{-1}$

NMR (CDCl$_3$, δ): 0.86 (6H, s), 0.89 (9H, s), 1.25 (6H, d, J=6.2 Hz), 1.98–2.13 (1H, m), 2.41–2.56 (1H, m), 3.21–3.31 (3H, m), 3.58–3.66 (3H, m), 3.76–3.80 (2H, m), 3.95–4.24 (4H, m), 4.42 (1H, t, J=4.1 Hz), 4.58–4.84 (5H, m), 5.20–5.49 (4H, m), 5.84–6.05 (2H, m)

EXAMPLE 16

Allyl (4R,5S,6S)-3-[(2S,4S)-1-allyloxycarbonyl-2-(2-fluoroethyloxymethyl)pyrrolidin-4-ylthio]-6-[(1R)-1-(tertbutyldimethylsilyloxy)ethyl]-4-methyl-7-oxo-1-azabicyclo-[3.2.0]hept-2-ene-2-carboxylate was obtained by reacting allyl (4R,5S,6S)-6-[(1R)-1-(tert-butyldimethylsilyloxy)ethyl]-4-methyl-3-benzylsulfinyl-7-oxo-1-azabicyclo-[3.2.0]hept-2-ene-2-carboxylate with (2S,4S)-1-allyloxycarbonyl-2-(2-fluoroethyloxymethyl)-4-mercaptopyrrolidine according to a similar manner to that of Example 15.

EXAMPLE 17

The following compounds were obtained according to a similar manner to that of Example 1 (1).

(1) (3S,4R)-3-[(1R)-1-(tert-Butyldimethylsilyloxy)ethyl]-4-[{(phenylthio)thiocarbonyl)methyl]-2-oxoazetidine NMR (CDCl$_3$, δ): 0.08 (6H, s), 0.88 (9H, s), 1.23 (3H, d, J=6.3 Hz), 2.90 (1H, m), 3.21 (1H, dd, J=15.0 and 9.0 Hz), 3.47 (1H, dd, J=15 and 3.9 Hz), 4.17–4.23 (2H, m), 6.10 (1H, s), 7.38–7.52 (5H, m)

(2) (3S,4R)-3-[(1R)-1-(tert-Butyldimethylsilyloxy)ethyl]-4-[{(methylthio)thiocarbonyl}methyl]-2-oxoazetidine IR (Neat): 3100, 1760 cm$^{-1}$ NMR (CDCl$_3$, δ): 0.06 (6H, s), 0.88 (9H, s), 1.20 (3H, d, J=6 Hz), 2.65 (3H, s), 2.88 (1H, m), 3.21 (1H, dd, J=14 and 9 Hz), 3.44 (1H, dd, J=14 and 4 Hz), 4.05–4.24 (2H, m), 6.09 (1H, s)

(3) (3S,4S)-4-[(1R)-1-{((2S,4S)-1-Allyloxycarbonyl-2-(dimethylcarbamoyl)pyrrolidin-4-ylthio)thiocarbonyl-}ethyl]-3-[(1R)-1-{(tert-butyldimethylsilyloxy)ethyl}-2-oxoazetidine IR (CHCl$_3$): 1755, 1700, 1655 cm$^{-1}$ NMR (CDCl$_3$, δ): 0.04 (6H, s), 0.86 (9H, s), 1.10 (3H, d, J=6.2 Hz), 1.35 (3H, d, J=6.7 Hz), 3.88 (1H, dd, J=2.1, 5.6 Hz)

EXAMPLE 18

To a suspension of anhydrous zinc chloride (56 mg) in acetonitrile (1.6 ml) cooled to 0° C. was added triethylamine (0.17 ml). After stirring for 10 minutes at 0° C., to the solution were added copper(I) chloride (41 mg), (3R,4R)-4-acetoxy-3-[(1R)-1-(tert-butyldimethylsilyloxy)ethyl]-2-oxoazetidine (79 mg) and phenyl dithiopropionate (75 mg). The reaction mixture was stirred at 0° C. for 2 hours. The mixture was poured into a stirred mixture of dichloromethane (5 ml) and 1N aqueous hydrochloric acid solution (5 ml). The organic layer was separated, washed with water, aqueous sodium bicarbonate solution and brine, and dried. The solution was concentrated under reduced pressure and the residue was purified by silica gel column chromatography (ethyl acetate:n-hexane=1:4, V/V) to afford a mixture (5:1) (77 mg) of (3S,4S)-3-[(1R)-1-(tert-butyldimethylsilyloxy)ethyl]-4-[(1R)-1-{(phenylthio)thiocarbonyl}ethyl]-2-oxoazetidine and (3S,4S)-3-[(1R)-1-(tert-butyldimethylsilyloxy)ethyl]-4-[(1S)-1-{(phenylthio)thiocarbonyl}ethyl]-2-oxoazetidine.

NMR (CDCl$_3$, δ): 0.07 (3H, s), 0.08 (3H, s), 0.89 (9H, s), 1.19 (3H, d, J=6.3 Hz), 1.42 (3H, d, J=6.8 Hz), 3.01 (1H, m), 3.62–3.68 (1H, m), 3.97 (1H, dd, J=5.5, 2.2 Hz), 4.14–4.25 (1H, m), 6.04 (1H, br s), 7.34–7.39 (2H, m), 7.48–7.51 (3H, m)

EXAMPLE 19

A mixture of (3S,4R)-3-[(1R)-1-(tertbutyldimethylsilyloxy)ethyl]-4-[(1-phenylthio-1-propenyl)thio]-2-oxoazetidine (mixture of E and Z isomers) (123 mg) and anhydrous zinc iodide (287 mg) in anhydrous acetonitrile was heated under reflux for 3 hours. The mixture was quenched by 1N aqueous hydrochloric acid solution and extracted with methylene chloride. The organic layer was dried and concentrated under reduced pressure. The residue was purified by silica gel column chromatography (ethyl acetate:n-hexane=1:4) to afford a mixture (5:1) (81 mg) of (3S,4S)-3-[(1R)-1-(tert-butyldimethylsilyloxy)ethyl]-4-[(1R)-1-{(phenylthio)thiocarbonyl}ethyl]-2-oxoazetidine and (3S,4S)-3-[(1R)-1-(tert-butyldimethylsilyloxy)ethyl]-4-[(1S)-1-{(phenylthio)-thiocarbonyl}ethyl]-2-oxoazetidine.

NMR (CDCl₃, δ): 0.07 (3H, s), 0.08 (3H, s), 0.89 (9H, s), 1.19 (3H, d, J=6.3 Hz), 1.42 (3H, d, J=6.8 Hz), 3.01 (1H, m), 3.62–3.68 (1H, m), 3.97 (1H, dd, J=5.5, 2.2 Hz), 4.14–4.25 (1H, m), 6.04 (1H, br s), 7.34–7.39 (2H, m), 7.48–7.51 (3H, m)

EXAMPLE 20

The following compounds were obtained according to a similar manner to that of Example 6(1).

(1) Mixture of (3S,4S)-1-[(1R)-1-(allyloxycarbonyl)-1-hydroxymethyl]-3-[(1R)-1-(tert-butyldimethylsilyloxy)ethyl]-4-[(1R)-1-{(phenylthio)thiocarbonyl}ethyl]-2-oxoazetidine and (3S,4S)-1-[(1S)-1-(allyloxycarbonyl)-1-hydroxymethyl]-3-[(1R)-1-(tert-butyldimethylsilyloxy)ethyl]-4-[(1R)-1-{(phenylthio)thiocarbonyl}ethyl]-2-oxoazetidine IR (Neat): 3100–3500 (br), 1750 cm⁻¹

(2) Mixture of (3S,4R)-1-[(1R)-1-(allyloxycarbonyl)-1-hydroxymethyl]-3-[(1R)-1-(tert-butyldimethylsilyloxy)ethyl]-4-[{(methylthio)thiocarbonyl}methyl]-2-oxoazetidine and (3S,4R)-1-[(1S)-1-allyloxycarbonyl)-1-hydroxymethyl]3-[(1R)-1-(tert-butyldimethylsilyloxy)ethyl]-4-[{(methylthio)thiocarbonyl}methyl]-2-oxoazetidine IR (Neat): 3400, 1770, 1750 cm⁻¹

NMR (CDCl₃, δ): 0.06 (6H, s), 0.86 (9H, s), 1.07–1.15 (3H, d, J=6 Hz), 2.62 (3H, s), 3.02–3.05 (1H, m), 3.27–3.55 (2H, m), 4.12–4.20 (1H, m), 4.15–4.80 (3H, m), 5.28–5.43 (3H, m), 5.86–5.97 (1H, m)

(3) Mixture of (3S,4S)-4-[(1R)-1-(((2S,4S)-1-allyloxycarbonyl-2-(dimethylcarbamoyl)pyrrolidin-4-ylthio)-thiocarbonyl}ethyl]-1-[(1R)-1-(allyloxycarbonyl)-1-hydroxymethyl]-3-[(1R)-1-tert-butyldimethylsilyloxy)ethyl]-2-oxoazetidine and (3S,4S)-4-[(1R)-1-{((2S,4S)-1allyloxycarbonyl-2-(dimethylcarbamoyl)pyrrolidin-4-ylthio)thiocarbonyl}ethyl]-1-[(1S)-1-(allyloxycarbonyl)-1-hydroxymethyl]-3-[(1R)-1-(tert-butyl-dimethylsilyloxy)ethyl]-2-oxoazetidine IR (CHCl₃): 3300, 1750, 1700, 1650 cm⁻¹

EXAMPLE 21

To a mixture of (3S,4S)-3-[(1R)-1-(tertbutyldimethyl-silyloxy)ethyl]-4-[(1R)-1-{(phenylthio)thiocarbonyl}ethyl]-2-oxoazetidine (100 mg) and cuprous chloride (30 mg) in acetonitrile (1 ml) was added (2S,4S)-1-allyloxycarbonyl-2-(dimethylcarbamoyl)-4-mercaptopyrrolidine (130 mg) and the mixture was stirred at the ambient temperature for 5 hours. The mixture was purified by preparative thin layer chromatography (developed with ethyl acetate) to give (3S,4S)-4-[(1R)-1-{((2S,4S)-1-allyloxycarbonyl-2-(dimethylcarbamoyl)pyrrolidin-4-ylthio)thiocarbonyl}ethyl]-3-[(1R)-1-(tertbutyldimethylsilyloxy)ethyl]-2-oxoazetidine (105 mg).

IR (CHCl₃): 1755, 1700, 1655 cm⁻¹

NMR (CDCl₃, δ): 0.04 (6H, s), 0.86 (9H, s), 1.10 (3H, d, J=6.2 Hz), 1.35 (3H, d, J=6.7 Hz), 3.88 (1H, dd, J=2.1, 5.6 Hz)

FAB-MS: 558 (M⁺ +1), 542, 514, 500, 426, 331

EXAMPLE 22

To a mixture of 2,6-dimethylpyridine (120 mg), ethyl acetate (5 ml) and a mixture (280 mg) of (3S,4S)-4-[(1R)-1-{((2S,4S)-1-allyloxycarbonyl-2-(dimethylcarbamoyl)pyrrolidin-4-ylthio)thiocarbonyl}ethyl]-1-[(1R)-1-allyloxycarbonyl-1-hydroxymethyl]-3-[(1R)-1-(tertbutyldimethylsilyloxy)ethyl]-2-oxoazetidine and (3S,4S)-4-[(1R)-1-{((2S,4S)-1-allyloxycarbonyl-2-(dimethylcarbamoyl)pyrrolidin-4-ylthio)thiocarbonyl}ethyl]-1-[(1S)-1-allyloxycarbonyl-1-hydroxymethyl]-3-[(1R)-1-(tert-butyldimethylsilyloxy)ethyl]-2-oxoazetidine was added a solution of thionyl chloride (100 mg) in ethyl acetate (0.5 ml) under ice-cooling, and the mixture was stirred for 20 minutes at the same temperature. Toluene (15 ml) was added to the reaction mixture and the mixture was filtered. The filtrate was evaporated under reduced pressure to give a residue.

The residue was dissolved in ethyl acetate (5 ml) and triphenylphosphine (328 mg) was added to the mixture. The mixture was cooled at −25 ~ −20° C., and sodium iodide (187 mg) was added thereto. The mixture was stirred at the same temperature for 15 minutes and allowed to stand at the ambient temperature for one hour. The mixture was washed with saturated aqueous sodium hydrogencarbonate and brine, dried over magnesium sulfate, and concentrated under reduced pressure to give a syrup. The syrup was subjected to a column chromatography on silica gel (10 g) and eluted with a mixture of hexane and ethyl acetate (1:1 and next, 2:3 (V/V)) to give (3S,4S)-4-[(1R)-1-{((2S,4S)-1-allyloxycarbonyl-2-(dimethylcarbamoyl)pyrrolidin-4-ylthio)thiocarbonyl}ethyl]-1-[1-(allyloxycarbonyl)-1-(triphenylphosphoranediyl)methyl]-3-[(1R)-1-(tertbutyldimethylsilyloxy)ethyl]-2-oxoazetidine (167 mg).

IR (CHCl₃): 1740, 1710–1695, 1665–1645 cm⁻¹

FAB-MS: 917 (M⁺ +1), 900, 858

EXAMPLE 23

The following compounds were obtained according to similar manners to those of Examples 9(1) and 22.

(1) (3S,4R)-1-[1-(Allyloxycarbonyl)-1-(triphenylphosphoranediyl)methyl]-3-[(1R)-1-(tertbutyldimethylsilyloxy)ethyl]-4-[{(methylthio)thiocarbonyl}methyl]-2-oxoazetidine IR (Nujol): 1740 cm⁻¹

NMR (CDCl₃, δ): 0.01 (6H, s), 0.77 (9H, s), 1.08–1.21 (3H, J=6 Hz), 2.66 (3H, s), 2.86–3.13 (1H, m), 3.20–3.62 (1H, m), 3.80 (1H, dd, J=14 and 8 Hz), 4.06–4.22 (1H, m), 4.43–4.68 (2H, m), 5.13–5.41 (2H, m), 5.91–6.08 (1H, m), 7.26–7.74 (15H, m)

(2) (3S,4S)-1-[1-(Allyloxycarbonyl)-1-(triphenylphosphoranediyl)methyl]-3-[(1R)-1-(tert-butyldimethylsilyloxy)ethyl]-4-[(1R)-1-{(phenylthio)thiocarbonyl}ethyl]-2-oxoazetidine IR (Nujol): 1620, 1740 cm⁻¹

NMR (CDCl₃, δ): 4.58–4.70 (2H, m), 5.21–5.47 (2H, m), 5.98 (1H, m)

EXAMPLE 24

To a mixture of (3S,4S)-3-[(1R)-1-(tertbutyldimethylsilyloxy)ethyl] -4-[(1R)-1-{(phenylthio)thiocarbonyl}ethyl]-2-oxoazetidine (5.12 g) in dichloromethane (50 ml) were added pyridine (1.8 ml) and allyl chloroglyoxylate (2.3 ml) successively at 0° C. After stirring for 2 hours at the same temperature, to the solution were added pyridine (0.9 ml) and allyl chloroglyoxylate (0.75 ml). After stirring for 1 hour at 0° C., the solution was washed with water, 1N hydrochloric acid and brine, and dried. The solvent was removed under reduced pressure and the residue was purified by column chromatography (ethyl acetate:hexane=1:9) to afford (3S,4S)-1-(allyloxyoxalyl)-3-[(1R)-1-(tert-butyldimethylsilyloxy)ethyl]-4-[(1R)-1-{(phenylthio)thiocarbonyl}ethyl]-2-oxoazetidine (4.77 g).

IR (Neat): 1705, 1755, 1808 cm⁻¹

NMR (CDCl₃, δ): 0.09 (6H, s), 0.83 (9H, s), 1.18 (3H, d, J=6.4 Hz), 1.48 (3H, d, J=6.8 Hz), 3.83 (1H, t, J=3.0 Hz), 4.21–4.34 (2H, m), 4.58–4.63 (1H, m), 4.79–4.84 (2H, m), 5.29–5.46 (2H, m), 5.87–6.08 (1H, m),

EXAMPLE 25

The following compound was obtained according to a similar manner to that of Example 24.

(3S,4S)-1-(Allyloxyoxalyl)-4-[(1R)-1-{((2S,4S)-1-allyloxycarbonyl-2-(dimethylcarbamoyl)pyrrolidin-4-ylthio)thiocarbonyl}ethyl]-3-[(1R)-1-(tert-butyldimethylsilyloxy)ethyl]-2-oxoazetidine IR (Neat): 1805, 1750, 1710–1700, 1660–1650 cm⁻¹

NMR (CDCl₃, δ): 0.05 (6H, s), 0.78 (9H, s), 1.10 (3H, d, J=6.3 Hz), 1.37 (3H, d, J=6.8 Hz)

FAB-MS: 670 (M⁺+1), 612, 586, 497, 383

EXAMPLE 26

The following compounds were obtained according to a similar manner to that of Example 10(1).

(1) Allyl (4R,5S,6S)-3-[(2S,4S)-1-allyloxycarbonyl-2-(dimethylcarbamoyl)pyrrolidin-4-ylthio]-6-[(1R)-1-(tert-butyldimethylsilyloxy)ethyl]-4-methyl-7-oxo-1-azabicyclo[3.2.0]hept-2-ene-2-carboxylate IR (CHCl₃) 1770, 1710–1695, 1660–1650 cm⁻¹

FAB-MS: 622 (M⁺+1), 606, 422, 262

(2) Allyl (4R,5S,6S)-3-phenylthio-6-[(1R)-1-tertbutyldimethylsilyloxy)ethyl]-4-methyl-7-oxo-1-azabicyclo[3.2.0]hept-2-ene-2-carboxylate IR (Neat): 1710, 1780 cm⁻¹

NMR (CDCl₃, δ): 1.18 (3H, d, J=6.2 Hz), 2.98–3.06 (1H, m), 3.13–3.17 (1H, m), 4.10–4.25 (2H, m), 4.75–4.83 (2H, m), 5.22–5.30 (1H, m), 5.43–5.52 (2H, m), 5.90–6.01 (1H, m), 7.27–7.56 (5H, m)

EXAMPLE 27

The following compounds were obtained according to a similar manner to that of Example 12(1).

(1) Allyl (5R,6S)-6-[(1R)-1-(tert-butyldimethylsilyloxy)ethyl]-3-methylthio-7-oxo-1-azabicyclo[3.2.0]hept-2-ene-2-carboxylate IR (Nujol): 1765, 1690 cm⁻¹

NMR (CDCl₃, δ): 0.08 (6H), s), 0.89 (9H, s), 1.26 (3H, d, J=6 Hz), 2.38 (3H, s), 2.96–3.29 (2H, m), 4.07–4.23 (2H, m), 4.67–4.78 (2H, m), 5.20–5.50 (2H, m), 5.87–6.03 (1H, m)

(2) Allyl (4R,5S,6S)-3-[(2S,4S)-1-allyloxycarbonyl-2-(dimethylcarbamoyl)pyrrolidin-4-ylthio]-6-[(1R)-1-(tert-butyldimethylsilyloxy)ethyl]-4-methyl-7-oxo-1-azabicyclo[3.2.0]hept-2-ene-2-carboxylate IR (CHCl₃): 1770, 1710–1695, 1660–1650 cm⁻¹

FAB-MS: 622 (M⁺+1), 606, 422, 262

(3) Allyl (4R,5S,6S)-3-phenylthio-6-[(1R)-1-(tert-butyldimethylsilyloxy)ethyl]-4-methyl-7-oxo-1-azabicyclo[3.2.0]hept-2-ene-2-carboxylate IR (Neat): 1710, 1780 cm⁻¹

NMR (CDCl₃, δ): 1.18 (3H, d, J=6.2 Hz), 2.98–3.06 (1H, m), 3.13–3.17 (1H, m), 4.10–4.25 (2H, m), 4.75–4.83 (2H, m), 5.22–5.30 (1H, m), 5.43–5.52 (2H, m), 5.90–6.01 (1H, m), 7.27–7.56 (5H, m)

EXAMPLE 28

Allyl (4R,5S,6S)-6-[(1R)-1-(tert-butyldimethylsilyloxy)ethyl]-4-methyl-3-methylthio-7-oxo-1-azabicyclo[3.2.0]hept-2-ene-2-carboxylate (100 mg) was added to a mixture of 70% aqueous tetrabutylammonium fluoride (0.71 g) and acetic acid (121 mg) in tetrahydrofuran (2 ml) and the mixture was allowed to stand at ambient temperature for 24 hours. The solution was diluted with ethyl acetate (6 ml), washed with water, aqueous sodium bicarbonate solution and brine, and dried. The solvent was removed off under reduced pressure and the residue was crystallized from n-hexane to afford allyl (4R,5S,6S)-6-((1R)-1-hydroxyethyl)-4-methyl-3-methylthio-7-oxo-1-azabicyclo[3.2.0]hept-2-ene-2-carboxylate (58.4 mg).

IR (Nujol): 3450, 1740 cm⁻¹

NMR (CDCl₃, δ): 1.25 (3H, d, J=7.3 Hz), 1.36 (3H, d, J=6.3 Hz), 2.40 (3H, s), 3.23 (1H, dd, J=7.1, 2.5 Hz), 3.41 (1H, m), 4.19 (1H, dd, J=9, 2.5 Hz), 4.17–4.29 (1H, m), 4.64–4.88 (2H, m), 5.40–5.50 (2H, m), 5.88–6.05 (1H, m)

EXAMPLE 29

The following compound was obtained according to a similar manner to that of Example 13 (1).

Allyl (4R,5S,6S)-3-phenylsulfinyl-6-[(1R)-1-(tert-butyldimethylsilyloxy)ethyl]-4-methyl-7-oxo-1-azabicyclo[3.2.0]hept-2-ene-2-carboxylate IR (Neat): 1580, 1728, 1788 cm⁻¹

NMR (CDCl₃, δ): 3.21–3.25 (1H, m), 4.36 (1H, dd, J=10.7 and 3.4 Hz), 5.91–6.00 (1H, m)

EXAMPLE 30

To a solution of allyl (4R,5S,6S)-6-((1R)-1-hydroxyethyl)-4-methyl-3-methylthio-7-oxo-1-azabicyclo[3.2.0]hept-2-ene-2-carboxylate (100 mg) in ethanol (1.0 ml) was added a 30% aqueous solution of hydrogen peroxide (0.5 ml) and the mixture was allowed to stand at the ambient temperature for 18 hours. The solution was diluted with methylene dichloride and washed with water, 5% aqueous sodium thiosulfate solution and brine successively. The organic layer was dried and concentrated under reduced pressure. The residue was purified by silica gel column chromatography to afford allyl (4R,5S,6S)-6-((1R)-1-hydroxyethyl)-4-methyl-3-methylsulfinyl-7-oxo-1-azabicyclo[3.2.0]hept-2-ene-2-carboxylate (50.0 mg).

IR (Neat): 3350, 1780, 1725 cm⁻¹

NMR (CDCl₃, δ): 1.33–1.40 (6H, m), 2.85 and 2.91 (1.9 and 1.1H, each s), 3.36–3.46 (1H, m), 3.32–3.94 (1H, m), 4.19–4.40 (3H, m), 4.65–4.86 (2H, m), 5.28–5.52 (2H, m), 5.52–6.03 (1H, m)

EXAMPLE 31

Allyl (4R,5S,6S)-3-[(2S,4S)-1-allyloxycarbonyl-2-(2-fluoroethyloxymethyl)pyrrolidin-4-ylthio]-6-[(1R)-1-tertbutyldimethylsilyloxy)ethyl]-4-methyl-7-oxo-1-azabicyclo[ 3.2.0]hept-2-ene-2-carboxylate was obtained by reacting allyl (4R,5S,6S)-3-phenylsulfinyl-6-[(1R)-1-(tertbutyldimethylsilyloxy)ethyl]-4-methyl-7-oxo-1-azabicyclo[3.2.0]hept-2-ene-2-carboxylate with (2S,4S)-1-allyloxycarbonyl-2-(2-fluoroethyloxymethyl)-4-mercaptopyrrolidine according to a similar manner to that of Example 15.

NMR (CDCl₃, δ): 0.86 (6H, s), 0.89 (9H, s), 1.25 (6H, d, J=6.2 Hz), 1.98–2.13 (1H, m), 2.41–2.56 (1H, m), 3.21–3.31 (3H, m), 3.58–3.66 (3H, m), 3.76–3.80 (2H, m), 3.95–4.24 (4H, m), 4.42 (1H, t, J=4.1 Hz), 4.58–4.84 (5H, m), 5.20–5.49 (4H, m), 5.84–6.05 (2H, m)

EXAMPLE 32

To a mixture of allyl (4R,5S,6S)-6-[(1R)-1-hydroxyethyl]-4-methyl-3-methylsulfinyl-7-oxo-1-azabicyclo[3.2.0]hept-2-ene-2-carboxylate (150 mg) and silica gel (300 mg) in N,N-dimethylformamide (1.5 ml) was added a solution of (2S,4S)-1-allyloxycarbonyl-2-(2- fluoroethoxymethyl)-4-mercaptopyrrolidine (150 mg) i dimethylacetamide (1.45 g). The mixture was stirred for 2 hours at ambient temperature. Silica gel was removed by filtration and the filtrate was concentrated under reduced pressure. The residue was purified by preparative thin layer chromatography to afford allyl (4R,5S,6S)-3-[(2S,4S)-1-allyloxycarbonyl-2-(2-fluoroethoxymethyl)pyrrolidin-4-ylthio]-6-[(1R)-1-hydroxyethyl]-4-methyl-7-oxo-1-azabicyclo[3.2.0]hept-2-ene-2-carboxylate (160 mg).

IR (Neat): 3450, 1775, 1690 cm$^{-1}$

NMR (CDCl$_3$, δ): 1.27 (3H, d, J=6 Hz), 1.36 (3H, d, J=6 Hz), 1.8–2.15 (1H, m), 2.30–2.70 (1H, m), 3.15–3.42 (3H, m), 3.45–3.90 (3H, m), 3.95–4.35 (6H, m), 4.41–4.43 (1H, m), 4.58–4.89 (5H, m), 5.20–5.49 (4H, m), 5.87–6.05 (2H, m)

What we claim is:
1. A compound of the formula:

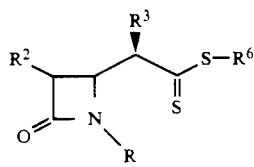

in which

R$^2$ is hydroxy (lower)alkyl or protected hydroxy(lower)alkyl,

R$^3$ is lower alkyl,

R$^6$ is lower alkyl;

mono(or di or tri)halo(lower)alkyl;

lower alkenyl;

lower alkynyl;

aryl which may have one to three substituent(s) selected from the group consisting of lower alkyl, halogen, hydroxy, protected hydroxy, lower alkenyl and lower alkynyl; or ar(lower)alkyl; and R is hydrogen, a group of the formula:

wherein R$^1$ is carboxy or protected carboxy, a group of the formula:

wherein R$^1$ is as defined above, and X$^2$ is halogen, a group of the formula:

wherein R$^1$ is as defined above, or a group of the formula:

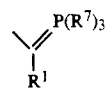

wherein R$^1$ is as defined above and R$^7$ is lower alkoxy or aryl, or a salt thereof.

2. The compound of claim 1, of the formula:

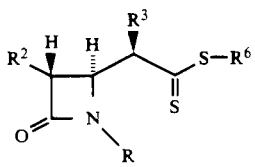

in which R, R$^2$, R$^3$ and R$^6$ are each as defined in claim 1.

3. The compound of claim 2, in which R$^6$ is lower alkyl, aryl, or ar(lower)alkyl.

4. The compound of claim 3, wherein R$^6$ is lower alkyl, phenyl, or phenyl)lower)alkyl.

* * * * *